(12) United States Patent
Hunter et al.

(10) Patent No.: US 7,303,870 B2
(45) Date of Patent: Dec. 4, 2007

(54) METHOD OF DETECTING MICROORGANISMS

(75) Inventors: Neil Hunter, Pennant Hills (AU); Nicholas A. Jacques, East Ryde (AU); Fjelda E. Martin, Oatlands (AU); Mangala A. Nadkarni, Ashfield (AU)

(73) Assignee: University of Sydney, Sydney (AU)

( * ) Notice: Subject to any disclaimer, the term of this patent is extended or adjusted under 35 U.S.C. 154(b) by 298 days.

(21) Appl. No.: 10/343,319

(22) PCT Filed: Jul. 27, 2001

(86) PCT No.: PCT/AU01/00933

§ 371 (c)(1), (2), (4) Date: Sep. 17, 2003

(87) PCT Pub. No.: WO02/10444

PCT Pub. Date: Feb. 7, 2002

(65) Prior Publication Data

US 2004/0072242 A1 Apr. 15, 2004

(30) Foreign Application Priority Data

Jul. 28, 2000 (AU) .................................... PQ9090

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/24.3

(58) Field of Classification Search ..................... None
See application file for complete search history.

(56) References Cited

OTHER PUBLICATIONS

Blok, H.J. et al., "Quantitative Analysis of 16SrDNA Using Competitive PCR and the QPCR System 5000", Biotechniques, vol. 22, pp. 700-702 and 704 (1997).*

* cited by examiner

*Primary Examiner*—Teresa E. Strzelecka
(74) *Attorney, Agent, or Firm*—Knobbe, Martens, Olson & Bear, LLP

(57) ABSTRACT

The present invention relates generally to a method for detecting, enumerating and/or identifying microorganisms in a sample. More particularly, the present invention provides a method for determining total microbial content in a sample by detecting the presence of nucleotide sequences associated with all or part of 16S rDNA or its corresponding 16S rRNA or its homologue, functional equivalent or derivative. The nucleotide sequences of the present invention may be used as an indicator of any microorganism and, hence, represents a universal target sequence which is indicative of total microbial content in a sample. The universal target sequence may also be varied to render same genus or species specific or the universal target used to trap microbial DNA or RNA which may be subsequently analyzed by sequence analysis or genetic probe technology. The universal target sequence is useful inter alia to design as universal primers and probes to amplify any microbial-derived genomic sequence, as a means to detect and enumerate total microorganisms and to identify microorganisms in a sample at the genus or species level. Such uses enable improved methods of enviroprotection, bioremediation, medical diagnosis and industrial microbiology. The present invention further relates to the universal target sequence in isolated form and/or primers or probes capable of hybridizing to same and kits for the detection of total microbial content in a sample.

28 Claims, 14 Drawing Sheets

| # | Organism | | | | |
|---|---|---|---|---|---|
| 1 | Bacteroides forsythus-AB035460 | CCCCACACTG | GTACTGAGAC | ACGGACCAGA | CTCCTACGGG AGGCAGCAGT |
| 2 | Porphyromonas gingivalis-POYRR16SC | CCCCACACTG | GTACTGAGAC | ACGGACCAGA | CTCCTACGGG AGGCAGCAGT |
| 3 | Prevotella melaninogenica-PVORR16SF | CCCCACATTG | GAACTGAGAC | ACGGTCCNAA | CTCCTACGGG AGGCAGCAGT |
| 4 | Cytophaga baltica-CBA5972 | AGTCACACTG | GTACTGAGAC | ACGGACCAGA | CTCCTACGGG AGGCAGCAGT |
| 5 | Campylobacter jejuni-CAJRRDAD | GGACACACTG | GAACTGAGAC | ACGGTCCAGA | CTCCTACGGG AGGCAGCAGT |
| 6 | Helicobacter pylori-HPU00679 | GGACACACTG | GGACTGAGAT | ACGGCCCAAA | CTCCTACGGG AGGCAGCAGC |
| 7 | Treponema denticola-AF139203 | GGACACACTG | GGACTGAGAC | ACGGCCCAGA | CTCCTACGGG AGGCAGCAGC |
| 8 | Treponema pallidum-TRPRG16S | AGCCACACTG | GGACTGAGAC | ACGGCCCAGA | CTCCTACGGG AGGCAGCAGT |
| 9 | Leptothrix mobilis-LM16SRR | CGTCACACTG | GGACTGAGAC | ACGGCCCAGA | CTCCTACGGG AGGCAGCAGT |
| 10 | Thiomicrospira denitrificans-TDE243144 | CGCCACACTG | GGACTGAGAC | ACGGCCCAGA | CTCCTACGGG AGGCAGCAGT |
| 11 | Neisseria meningitidis-AF059671 | AGCCACACCG | GGACTGAGAC | ACGGCCCNGN | CTCCTACGGG AGGCAGCAGT |
| 12 | Actinobacillus actinomycetemcomitans-ACNRRNAJ | AGCCACACTG | GAACTGAGAC | ACGGTCCAGA | CTCCTACGGG AGGCAGCAGT |
| 13 | Haemophilus influenzae-HIDNA5483 | AGCAACACTG | GAACTGAGAC | ACGGTCCAGA | CTCCTACGGG AGGCAGCAGT |
| 14 | Escherichia coli-ECAT1177T | AGCCACACTG | GAACTGAGAC | ACGGTCCAGA | CTCCTACGGG AGGCAGCAGT |
| 15 | Salmonella typhi-STRNA16 | AGCCACACTG | GAACTGAGAC | ACGGCCCAGA | CTCCTACGGG AGGCAGCAGT |
| 16 | Vibrio cholerae-VC16SRRNA | AGCCACACTG | GGACTGAGAC | ACGGCCCAGA | CTCCTACGGG AGGCAGCAGT |
| 17 | Coxiella burnetii-D89791 | AGCCACACTG | GAACTGAGAC | ACGGTCCAGA | CTCCTACGGG AGGCAGCAGT |
| 18 | Legionella pneumophila-LP16SRNA | AGCCACATTG | GGACTGAGAT | ACGGCCCAGA | CTCCTACGGG AGGCAGCAGT |
| 19 | Pseudomonas aeruginosa-PARN16S | AGTCACACTG | GGACTGAGAC | ACGGTCCAGA | CTCCTACGGG AGGCAGCAGT |
| 20 | Caulobacter vibrioides-CVI009957 | AGCCACACTG | GGACTGAGAC | ACGGCCCAAA | CTCCTACGGG AGGCAGCAGT |
| 21 | Rhodospirillum rubrum-RR16S107R | AGCCACACTG | GGACTGAGAC | ACGGCCCAGA | CTCCTACGGG AGGCAGCAGT |
| 22 | Nitrobacter winogradskyi-NIT16SRA | AGCCACACTG | GGACTGAGAT | ACGGTCCAGA | CTCCTACGGG AGGCAGCAGT |
| 23 | Wolbachia species-WSP010275 | AGCCACACTG | GAACTGAGAC | ACGGTCCAGA | CTCCTACGGG AGGCAGCAGT |
| 24 | Myxococcus xanthus-MXA233930 | AGCCACACTG | GAACTGAGAC | ACGGCCCAGA | CTCCTACGGG AGGCAGCAGT |
| 25 | Corynebacterium diphtheriae-CD16SRDNA | GGCCACATTG | GGACTGAGAT | ACGGCCCAGA | CTCCTACGGG AGGCAGCAGT |
| 26 | Mycobacterium tuberculosis-MTRRNOP | GGCCACACTG | GGACTGAGAT | ACGGCCCAGA | CTCCTACGGG AGGCAGCAGT |
| 27 | Streptomyces coelicolor-SC16SRNA | GGCCACACTG | GGACTGAGAC | ACGGCCCAGA | CTCCTACGGG AGGCAGCAGT |
| 28 | Actinomyces odontolyticus-AO16SRD | GGTCACATTG | GGACTGAGAT | ACGGCCCAGA | CT. CTACGGG AGGCAGCAGT |
| 29 | Bacillus subtilis-AB016721 | GGCCACACTG | GGACTGAGAT | ACGGCCCAGA | CTCCTACGGG AGGCAGCAGT |
| 30 | Staphylococcus aureus-SA16SRRN | GGCCACACTG | GAACTGAGAC | ACGGTCCAGA | CTCCTACGGG AGGCAGCAGT |
| 31 | Listeria monocytogenes-S55472 | GGCCACACTG | GGACTGAGAC | ACGGCCCAGA | CTCCTACGGG AGGCAGCAGT |
| 32 | Enterococcus faecalis-AB012212 | GGCCACACTG | GGACTGAGAC | ACGGCCCAGA | CTCCTACGGG AGGCAGCAGT |
| 33 | Lactobacillus acidophilus-LBARR16SAZ | GGCCACATTG | GGACTGAGAC | ACGGCCCAAA | CTCCTACGGG AGGCAGCAGT |
| 34 | Streptococcus mutans-SM16SRNA | GGCCACACTG | GAACTGAGAC | ACGGCCCAGA | CTCCTACGGG AGGCAGCAGT |
| 35 | Clostridium botulinum-CBA16S | GGCCACATTG | GAACTGAGAC | ACGGTCCAGA | CTCCTACGGG AGGCAGCAGT |
| 36 | Peptostreptococcus micros-PEP16SRR8 | GGCCACATTG | GGACTGAGAC | ACGGTCCAAA | CT. CTACGGG AGGCAGCAGT |
| 37 | Veillonella dispar-VDRRNA16S | GGCCACATTG | GGACTGAGAC | ACGGCCCAAA | CTCCTACGGG AGGCAGCAGT |
| 38 | Fusobacterium nucleatum-X55401 | GGCCACAAGG | GGACTGAGAC | ACGGCCCNNA | CTCCTACGGG AGGCNGCNGT |
| 39 | Chlamydia trachomatis-D89067 | GCCACACTG | GGACTGAGAC | ACTGCCCAGA | CTCCTACGGG AGGCTGCAGT |
| 40 | Mycoplasma pneumoniae-AF132741 | AGCCACAATG | GGACTGAGAC | ACGGCCCATA | CTCCTACGGG AGGCAGCAGT |

FIGURE 1A

| | | | | | |
|---|---|---|---|---|---|
| 1 | B.forsythus-AB035460 | GCTAACTCCG | TGCCAGCAGC | CGCGGTAATA | CGGAGGATGC | GAGCGTTATC |
| 2 | P.gingivalis-POYRR16SC | GCTAACTCCG | TGCCAGCAGC | CGCGGTAATA | CGGAGNATGC | NAGCGTTATC |
| 3 | P.melaninogenica-PVORR16SF | GCTAATTCCG | TGCCAGCAGC | CGCGGTNATA | CGGAAGGTCC | NGGCGTTATC |
| 4 | C.baltica-CBA5972 | GCTAACTCCG | TGCCAGCAGC | CGCGGTAATA | CGGATGGTCC | GACCGTTATC |
| 5 | C.jejuni-CAJRRDAD | GCTAACTCCG | TGCCAGCAGC | CGCGGTAATA | CGGAGGGTGC | AAGCGTTACT |
| 6 | H.pylori-HPU00679 | GCTAACTCCG | TGCCAGCAGC | CGCGGTAATA | CGGAGGGTGC | AAGCGTTACT |
| 7 | T.denticola-AF139203 | GCTAATTACG | TGCCAGCAGC | CGCGGTAACA | CGTAAGGGGC | GAGCGTTGTT |
| 8 | T.pallidum-TRPRG16S | GCTAATTACG | TGCCAGCAGC | CGCGGTAACA | CGTAAGGGGC | GAGCGTTGTT |
| 9 | L.mobilis-LM16SRR | GCTAACTACG | TGCCAGCAGC | CGCGGTAATA | CGTAGGGTGC | AAGCGTTAAT |
| 10 | T.denitrificans-TDE243144 | GCTAACTACG | TGCCAGCAGC | CGCGGTAATA | CGTAGGGTGC | GAGCGTTAAT |
| 11 | N.meningitidis-AF059671 | GCTAACTACG | TGCCAGCAGC | CGCGGTAATA | CGTAGGGTGC | GAGCGTTAAT |
| 12 | A.actinomycetemcomitans-ACNRRNAJ | GCTAACTCCG | TGCCAGCAGC | CGCGGTAATA | CGGGGGGTGC | GAGCGTTAAT |
| 13 | H.influenzae-HIDNA5483 | GCTAACTCCG | TGCCAGCAGC | CGCGGTAATA | CGGAGGGTGC | GAGCGTTAAT |
| 14 | E.coli-ECAT1177T | GCTAACTCCG | TGCCAGCAGC | CGCGGTAATA | CGGAGGGTGC | AAGCGTTAAT |
| 15 | S.typhi-STRNA16 | GCTAACTCCG | TGCCAGCAGC | CGCGGTAATA | CGGAGGGTGC | AAGCGTTAAT |
| 16 | V.cholerae-VC16SRRNA | GCTAACTCTG | TGCCAGCAGC | CGCGGTAATA | CAGAGAGTGC | AAGCGTTAAT |
| 17 | C.burnetii-D89791 | GCTAACTCCG | TGCCAGCAGC | CGCGGTAATA | CGGAGGGTGC | GAGCGTTAAT |
| 18 | L.pneumophila-Lp16SRNA | GCTAACTTCG | TGCCAGCAGC | CGCGGTAATA | CGAAGGGTGC | AAGCGTTAAT |
| 19 | P.aeruginosa-PARN16S | GCTAACTTCG | TGCCAGCAGC | CGCGGTAATA | CGAAGGGTGC | AAGCGTTGCT |
| 20 | C.vibrioides-CVI009957 | GCTAACTTCG | TGCCAGCAGC | CGCGGTAATA | CGAAGGGGGC | TAGCGTTGCT |
| 21 | R.rubrum-RR16S107R | GCTAACTTCG | TGCCAGCAGC | CGCGGTAATA | CGAAGGGGGC | AAGCGTTGTT |
| 22 | N.winogradskyi-NIT16SRA | GCTAACTTCG | TGCCAGCAGC | CGCGGTAATA | CGAAGGGGGC | TAGCGTTGCT |
| 23 | Wolbachia.sp-WSP010275 | GCTAACTCCG | TGCCAGCAGC | CGCGGTAATA | CGGAGAGGGC | TAGCGTTATT |
| 24 | M.xanthus-MXA233930 | GCTAACTCTG | TGCCAGCAGC | CGCGGTAATA | CAGAGGGTGC | AAGCGTTGTT |
| 25 | C.diphtheriae-CD16SRDNA | GCCAACTACG | TGCCAGCAGC | CGCGGTAATA | CGTAGGGTGC | GAGCGTTGTC |
| 26 | M.tuberculosis-MTRRNOP | GCTAACTACG | TGCCAGCAGC | CGCGGTAATA | CGTAGGGTGC | AAGCGTTGTC |
| 27 | S.coelicolor-SC16SRNA | GCTAACTACG | TGCCAGCAGC | CGCGGTAATA | CGTAGGCGC | AAGCGTTGTC |
| 28 | A.odontolyticus-AO16SRD | GCTAACTACG | TGCCAGCAGC | CGCGGTAATA | CGTAGGGCGC | NAGCGTTGTC |
| 29 | B.subtilis-AB016721 | GCTAACTACG | TGCCAGCAGC | CGCGGTAATA | CGTAGGTGGC | AAGCGTTGTC |
| 30 | S.aureus-SA16SRRN | GCTAACTACG | TGCCAGCAGC | CGCGGTAATA | CGTAGGTGGC | AAGCGTTATC |
| 31 | L.monocytogenes-S55472 | GCTAACTACG | TGCCAGCAGC | CGCGGTAATA | CGTAGGTGGC | AAGCGTTGTC |
| 32 | E.faecalis-AB012212 | GCTAACTACG | TGCCAGCAGC | CGCGGTAATA | CGTAGGTGGC | AAGCGTTGTC |
| 33 | L.acidophilus-LBARR16SAZ | GCTAACTACG | TGCCAGCAGC | CGCGGTAATA | CGTAGGTGGC | AAGCGTTGTC |
| 34 | S.mutans-SM16SRNA | GCTNACTACG | TGCCAGCAGC | CGCGGTAATA | CGTAGGTCCC | NAGCGTTGTC |
| 35 | C.botulinum-CBA16S | GCTAACTACG | TGCCAGCAGC | CGCGGTAATA | CGTAGGTGGC | GAGCGTTGTC |
| 36 | P.micros-PEP16SRR8 | GCTAAATACG | TGCCAGCAGC | CGCGGTAATA | CGTATGGGGC | GAGCGTTGTC |
| 37 | V.dispar-VDRRNA16S | GCTAACTACG | TGCCAGCAGT | CGCGGTAATA | CGTAGGTGGC | AAGCGTTGTC |
| 38 | F.nucleatum-X55401 | GCTAAATACG | TGCCAGCAGC | CGCGGTAATA | CGTATGTCAC | NAGCGTTATC |
| 39 | C.trachomatis-D89067 | GCTAACTCCG | TGCCAGCAGC | CGCGGTAATA | CGGAGGGTGC | TAGCGTTAAT |
| 40 | M.pneumoniae-AF132741 | ACTAACTATG | TGCCAGCAGT | CGCGGTAATA | CATAGGTCGC | AAGCGTTATC |

| # | Organism | Sequence |
|---|---|---|
| 1 | B.forsythus-AB035460 | ACGAAAGCGT GGGTATCAAA CAGGATTAGA TACCCTGGTA GTCCACGCCAG |
| 2 | P.gingivalis-POYRR16SC | ACGAAGGCGT GGGTATCAAA CAGGATTAGA TACCCTGGTA GTCCACGCCAG |
| 3 | P.melaninogenica-PVORR16SF | TCGAAGGTGC GGGTATCAAA CAGGATTAGA TACCCTGGTA GTCCGCACAG |
| 4 | C.baltica-CBA5972 | ACGAAAGCGT GGGTAGCGAA CAGGATTAGA TACCCTGGTA GTCCACGCCG |
| 5 | C.jejuni-CAJRRDAD | GCGAAAGCGT GGGGAGCAAA CAGGATTAGA TACCCTGGTA GTCCACGCCC |
| 6 | H.pylori-HPU00679 | GCGAAAGCGT GGGGAGCAAA CAGGATTAGA TACCCTGGTA GTCCACGCCC |
| 7 | T.denticola-AF139203 | ACGAAGGTGC GGGGAGCGAA CAGGATTAGA TACCCTGGTA GTCCGCACAG |
| 8 | T.pallidum-TRPRG16S | GCGAAGGTGT GGGGAGCGAA CAGGATTAGA TACCCTGGTA GTCCACACAG |
| 9 | L.mobilis-LM16SRR | ACGAAAGCGT GGGGAGCAAA CAGGATTAGA TACCCTGGTA GTCCACCCCC |
| 10 | T.denitrificans-TDE243144 | ACGAAAGCGT GGGTAGCAAA CAGGATTAGA TACCCTGTA GTCCACGCCC |
| 11 | N.meningitidis-AF059671 | CCGAAAGCGT GGGTAGCAAA CAGGATTAGA TACCCTGGTA GTCCACGCCC |
| 12 | A.actinomycetemcomitans-ACNRRNAJ | GCGAAAGCGT GGGGAGCGAA CAGGATTAGA TACCCTGGTA GTCCACGCTG |
| 13 | H.influenzae-HIDNA5483 | GCGAAAGCGT GGGGAGCAAA CAGGATTAGA GACCCTGGTA GTCCACGCCG |
| 14 | E.coli-ECAT1177T | GCGAAAGCGT GGGGAGCAAA CAGGATTAGA TACCCTGGTA GTCCACGCCG |
| 15 | S.typhi-STRNA16 | GCGAAAGCGT GGGGAGCAAA CAGGATTAGA TACCCTGGTA GTCCACGCCG |
| 16 | V.cholerae-VC16SRRNA | ACGAAAGCGT GGGGAGCAAA CAGGATTAGA TACCCTGGTA GTCCACGCTG |
| 17 | C.burnetii-D89791 | GCGAAAGCGT GGGGAGCAAA CAGGATTAGA TACCCTGGTA GTCCACGCCG |
| 18 | L.pneumophila-LP16SRNA | TCGAAAGCGT GGGGAGCAAA CAGGATTAGA TACCCTGGTA GTCCACGCCG |
| 19 | P.aeruginosa-PARN16S | GCGAAAGCGT GGGGAGCAAA CAGGATTAGA TACCCTGGTA GTCCACGCCG |
| 20 | C.vibrioides-CVI009957 | ACGAAAGCGT GGGGAGCAAA CAGGATTAGA TACCCTGGTA GTCCACGCTG |
| 21 | R.rubrum-RR16S107R | GCGAAAGCGT GGGGAGCAAA CAGGATTAGA TACCCTGGTA GTCCACGCCC |
| 22 | N.winogradskyi-NIT16SRA | GCGAAAGCAT GGGGAGCGAA CAGGATTAGA TACCCTGGTA GTCCACGCCG |
| 23 | wolbachia.sp-WSP010275 | GCGAAAGCGT GGGGAGCAAA CAGGATTAGA TACCCTGGTA GTCCACGCCC |
| 24 | M.xanthus-MXA233930 | GCGAAAGCGT GGGGAGCGAA CAGGATTAGA TACCCTGGTA GTCCACGCCC |
| 25 | C.diphtheriae-CD16SRDNA | GCGAAAGCGT GGGGAGCGAA CAGGATTAGA TACCCTGGTA GTCCATGCCG |
| 26 | M.tuberculosis-MTRRNOP | GCGAAAGCGT GGGGAGCAAA CAGGATTAGA TACCCTGGTA GTCCACGCCG |
| 27 | S.coelicolor-SC16SRNA | GCGAAAGGCT GGGGAGCGAA CAGGATTAGA TACCCTGGTA GTCCACGCCG |
| 28 | A.odontolyticus-AO16SRD | GCGAAAGCGT GGGGAGCAAA CAGGATTAGA TACCCTGGTG GTCCACGCTG |
| 29 | B.subyilis-AB016721 | GCGAAAGCGT GGGGAGCAAA CAGGATTAGA TACCCTGGTA GTCCACGCCG |
| 30 | S.aureus-SA16SRRN | GCGAAAGCGT GGGGATCAAA CAGGATTAGA TACCCTGGTA GTCCACGCCG |
| 31 | L.monocytogenes-S55472 | GCGAAAGCGT GGGGAGCAAA CAGGATTAGA TACCCTGGTA GTCCACGCCG |
| 32 | E.faecalis-AB012212 | GCGAAAGCGT GGGGAGCAAA CAGGATTAGA TACCCTGGTA GTCCACGCCG |
| 33 | L.acidophilus-LBARR16SAZ | TCGAAAGCAT GGTAGCAAA CAGGATTAGA TACCCTGGTA GTCCACGCCG |
| 34 | S.mutans-SM16SRNA | TCGAAAGCAT GGGGAGCAAA CAGGATTAGA TACCCTGGTA GTCCATGCCG |
| 35 | C.botulinum-CBA16S | ACGAAAGCGT GGGTAGCAAA CAGGATTAGA TACCCTNGTA GTCCACGCCG |
| 36 | P.micros-PEP16SRRB | ACGAAAGCGT GGGTAGCAAA CAGGATTAGA TACCCTGGTA GTCCACGCTG |
| 37 | V.dispar-VDRRNA16S | GCGAAAGCCA GGGGAGCGAA CGGGATTAGA TACCCCGGTA GTCCACGCCG |
| 38 | F.nucleatum-X55401 | GCGAAAGCGT GGTAGCAAA CAGGATTAGA TACCCTGGTA GTCCTGCCG |
| 39 | C.trachomatis-D89067 | GCGAAAGCAA GGGGAGCAAA CAGGATTAGA TACCCTGGTA GTCCTTGCCG |
| 40 | M.pneumoniae-AF132741 | TTGAAAGTGT GGGGAGCAAA TAGGATTAGA TACCCTAGTA GTCCACACCG |

FIGURE 1C

SEQUENCE LISTING

<160> NUMBER OF SEQ ID NOS: 106

<210> SEQ ID NO 1
<211> LENGTH: 35
<212> TYPE: DNA

```
<213> ORGANISM: Artificial Sequence
<220> FEATURE:
<223> OTHER INFORMATION: probe.

<400> SEQUENCE: 1
tcccgttaca aaatcgtgtt tacatcgtat actcg                                35

<210> SEQ ID NO 2
<211> LENGTH: 26
<212> TYPE: DNA
<213> ORGANISM: Artificial Sequence
<220> FEATURE:
<223> OTHER INFORMATION: Primer.

<400> SEQUENCE: 2
ggactaccag ggtatctaat cctgtt                                          26

<210> SEQ ID NO 3
<211> LENGTH: 23
<212> TYPE: DNA
<213> ORGANISM: Artificial Sequence
<220> FEATURE:
<223> OTHER INFORMATION: Probe.

<400> SEQUENCE: 3
cgtattaccg cggctgctgg cac                                             23

<210> SEQ ID NO 4
<211> LENGTH: 23
<212> TYPE: DNA
<213> ORGANISM: Artificial Sequence
<220> FEATURE:
<223> OTHER INFORMATION: Primer.

<400> SEQUENCE: 4
ggaaggtaag ttgcatttca gca                                             23

<210> SEQ ID NO 5
<211> LENGTH: 30
<212> TYPE: DNA
<213> ORGANISM: Artificial Sequence
<220> FEATURE:
<223> OTHER INFORMATION: Primer.

<400> SEQUENCE: 5
gcgtacttat catggtaaat taagtcaatt                                      30

<210> SEQ ID NO 6
<211> LENGTH: 19
<212> TYPE: DNA
<213> ORGANISM: Artificial Sequence
<220> FEATURE:
<223> OTHER INFORMATION: Primer.

<400> SEQUENCE: 6
tcctacggga ggcagcagt                                                  19

<210> SEQ ID NO 7
<211> LENGTH: 21
<212> TYPE: DNA
<213> ORGANISM: Artificial Sequence
<220> FEATURE:
<223> OTHER INFORMATION: Primer.

<400> SEQUENCE: 7
tcggtaagtc agcggtgaaa c                                               21
```

-continued

```
<210> SEQ ID NO 8
<211> LENGTH: 18
<212> TYPE: DNA
<213> ORGANISM: Artificial Sequence
<220> FEATURE:
<223> OTHER INFORMATION: Primer.

<400> SEQUENCE: 8
gcaagctgcc ttcgcaat                                                 18

<210> SEQ ID NO 9
<211> LENGTH: 25
<212> TYPE: DNA
<213> ORGANISM: Artificial Sequence
<220> FEATURE:
<223> OTHER INFORMATION: Probe.

<400> SEQUENCE: 9
ctcaacgttc agcctgccgt tgaaa                                         25

<210> SEQ ID NO 10
<211> LENGTH: 50
<212> TYPE: DNA
<213> ORGANISM: Bacteroides forsythus
<220> FEATURE:
<221> NAME/KEY: misc_feature
<222> LOCATION: (0)...(0)
<223> OTHER INFORMATION: Also Porphyromonas gingivalis and Cytophaga
      baltica.

<400> SEQUENCE: 10
ccccacactg gtactgagac acggaccaga ctcctacggg aggcagcagt              50

<210> SEQ ID NO 11
<211> LENGTH: 50
<212> TYPE: DNA
<213> ORGANISM: Prevotella melaninogenica
<220> FEATURE:
<221> NAME/KEY: misc_feature
<222> LOCATION: 28
<223> OTHER INFORMATION: n = A,T,C or G

<400> SEQUENCE: 11
ccccacattg gaactgagac acggtccnaa ctcctacggg aggcagcagt              50

<210> SEQ ID NO 12
<211> LENGTH: 50
<212> TYPE: DNA
<213> ORGANISM: Campylobacter jejuni

<400> SEQUENCE: 12
agtcacactg gaactgagac acggtccaga ctcctacggg aggcagcagt              50

<210> SEQ ID NO 13
<211> LENGTH: 50
<212> TYPE: DNA
<213> ORGANISM: Helicobacter pylori

<400> SEQUENCE: 13
ggacacactg gaactgagac acggtccaga ctcctacggg aggcagcagt              50

<210> SEQ ID NO 14
<211> LENGTH: 50
<212> TYPE: DNA
<213> ORGANISM: Treponema denticola
```

```
<400> SEQUENCE: 14
ggacacattg ggactgagat acggcccaaa ctcctacggg aggcagcagc          50

<210> SEQ ID NO 15
<211> LENGTH: 50
<212> TYPE: DNA
<213> ORGANISM: Treponema pallidum

<400> SEQUENCE: 15
ggacacactg ggactgagat acggcccaga ctcctacggg aggcagcagc          50

<210> SEQ ID NO 16
<211> LENGTH: 50
<212> TYPE: DNA
<213> ORGANISM: Leptothrix mobilis

<400> SEQUENCE: 16
agccacactg ggactgagac acggcccaga ctcctacggg aggcagcagt          50

<210> SEQ ID NO 17
<211> LENGTH: 50
<212> TYPE: DNA
<213> ORGANISM: Thiomicrospira denitrificans

<400> SEQUENCE: 17
cgtcacactg ggactgagac acggcccaga ctcctacggg aggcagcagt          50

<210> SEQ ID NO 18
<211> LENGTH: 50
<212> TYPE: DNA
<213> ORGANISM: Neisseria meningitidis

<400> SEQUENCE: 18
cgccacactg ggactgagac acggcccaga ctcytacggg aggcagcagt          50

<210> SEQ ID NO 19
<211> LENGTH: 50
<212> TYPE: DNA
<213> ORGANISM: Actinobacillus actinomycetemcomitans
<220> FEATURE:
<221> NAME/KEY: misc_feature
<222> LOCATION: 28, 30
<223> OTHER INFORMATION: n = A,T,C or G

<400> SEQUENCE: 19
agccacaccg ggactgagac acggcccngn ctcctacggg aggcagcagt          50

<210> SEQ ID NO 20
<211> LENGTH: 50
<212> TYPE: DNA
<213> ORGANISM: Haemophilus influenzae

<400> SEQUENCE: 20
agccacactg gaactgagac acggtccaga ctcctacggg aggcagcagt          50

<210> SEQ ID NO 21
<211> LENGTH: 50
<212> TYPE: DNA
<213> ORGANISM: Escherichia coli

<400> SEQUENCE: 21
agcaacactg gaactgagac acggtccaga ctcctacggg aggcagcagt          50
```

<210> SEQ ID NO 22
<211> LENGTH: 50
<212> TYPE: DNA
<213> ORGANISM: Salmonella typhi
<220> FEATURE:
<221> NAME/KEY: misc_feature
<222> LOCATION: (0)...(0)
<223> OTHER INFORMATION: Also Myxococcus xanthus and Legionella pneumophila.

<400> SEQUENCE: 22
agccacactg gaactgagac acggtccaga ctcctacggg aggcagcagt          50

<210> SEQ ID NO 23
<211> LENGTH: 50
<212> TYPE: DNA
<213> ORGANISM: Vibrio cholerae

<400> SEQUENCE: 23
agccacactg gaactgagac acggtccaga ctcctacggg aggcagcagt          50

<210> SEQ ID NO 24
<211> LENGTH: 50
<212> TYPE: DNA
<213> ORGANISM: Coxiella burnetii

<400> SEQUENCE: 24
agccacactg ggactgagac acggcccaga ctcctacggg aggcagcagt          50

<210> SEQ ID NO 25
<211> LENGTH: 50
<212> TYPE: DNA
<213> ORGANISM: Pseudomonas aeruginosa

<400> SEQUENCE: 25
agtcacactg gaactgagac acggtccaga ctcctacggg aggcagcagt          50

<210> SEQ ID NO 26
<211> LENGTH: 50
<212> TYPE: DNA
<213> ORGANISM: Caulobacter vibrioides
<220> FEATURE:
<221> NAME/KEY: misc_feature
<222> LOCATION: (0)...(0)
<223> OTHER INFORMATION: Also Nitrobacter winogradskyi.

<400> SEQUENCE: 26
agccacattg ggactgagac acggcccaaa ctcctacggg aggcagcagt          50

<210> SEQ ID NO 27
<211> LENGTH: 50
<212> TYPE: DNA
<213> ORGANISM: Wolbachia species

<400> SEQUENCE: 27
agccacactg gaactgagat acggtccaga ctcctacggg aggcagcagt          50

<210> SEQ ID NO 28
<211> LENGTH: 50
<212> TYPE: DNA
<213> ORGANISM: Corynebacterium diphtheriae

<400> SEQUENCE: 28
ggccacattg ggactgagat acggcccaga ctcctacggg aggcagcagt          50

```
<210> SEQ ID NO 29
<211> LENGTH: 50
<212> TYPE: DNA
<213> ORGANISM: Mycobacterium tuberculosis

<400> SEQUENCE: 29
ggccacactg ggactgagat acggcccaga ctcctacggg aggcagcagt         50

<210> SEQ ID NO 30
<211> LENGTH: 50
<212> TYPE: DNA
<213> ORGANISM: Streptomyces coelicolor
<220> FEATURE:
<221> NAME/KEY: misc_feature
<222> LOCATION: (0)...(0)
<223> OTHER INFORMATION: Also Listeria monocytogenes.

<400> SEQUENCE: 30
ggccacactg ggactgagac acggcccaga ctcctacggg aggcagcagt         50

<210> SEQ ID NO 31
<211> LENGTH: 50
<212> TYPE: DNA
<213> ORGANISM: Actinomyces odontolyticus
<220> FEATURE:
<221> NAME/KEY: misc_feature
<222> LOCATION: (0)...(0)

<400> SEQUENCE: 31
ggtcacattg ggactgagat acggcccaga ctcctacggg aggcagcagt         50

<210> SEQ ID NO 32
<211> LENGTH: 50
<212> TYPE: DNA
<213> ORGANISM: Bacillus subtilis
<220> FEATURE:
<221> NAME/KEY: misc_feature
<222> LOCATION: (0)...(0)
<223> OTHER INFORMATION: Also Streptococcus mutans.

<400> SEQUENCE: 32
ggccacactg ggactgagac acggcccaga ctcctacggg aggcagcagt         50

<210> SEQ ID NO 33
<211> LENGTH: 50
<212> TYPE: DNA
<213> ORGANISM: Staphylococcus aureus

<400> SEQUENCE: 33
ggccacactg gaactgagac acggtccaga ctcctacggg aggcagcagt         50

<210> SEQ ID NO 34
<211> LENGTH: 49
<212> TYPE: DNA
<213> ORGANISM: Enterococcus faecalis

<400> SEQUENCE: 34
ggccacactg ggactgagac acggcccaga ctctacggga ggcagcagt          49

<210> SEQ ID NO 35
<211> LENGTH: 50
<212> TYPE: DNA
<213> ORGANISM: Lactobacillus acidophilus

<400> SEQUENCE: 35
```
ggccacattg ggactgagac acggcccaaa ctcctacggg aggcagcagt    50

<210> SEQ ID NO 36
<211> LENGTH: 50
<212> TYPE: DNA
<213> ORGANISM: Clostridium botulinum

<400> SEQUENCE: 36
ggccacattg gaactgagac acggtccaga ctcctacggg aggcagcagt    50

<210> SEQ ID NO 37
<211> LENGTH: 49
<212> TYPE: DNA
<213> ORGANISM: Peptostreptococcus micros

<400> SEQUENCE: 37
ggccacattg ggactgagac acggtccaaa ctcctacggga ggcagcagt    49

<210> SEQ ID NO 38
<211> LENGTH: 50
<212> TYPE: DNA
<213> ORGANISM: Veillonella dispar

<400> SEQUENCE: 38
ggccacattg ggactgagac acggcccaga ctcctacggg aggcagcagt    50

<210> SEQ ID NO 39
<211> LENGTH: 50
<212> TYPE: DNA
<213> ORGANISM: Fusobacterium nucleatum
<220> FEATURE:
<221> NAME/KEY: misc_feature
<222> LOCATION: 28, 29, 45, 48
<223> OTHER INFORMATION: n = A,T,C or G

<400> SEQUENCE: 39
ggccacaagg ggactgagac acggcccnna ctcctacggg aggcngcngt    50

<210> SEQ ID NO 40
<211> LENGTH: 50
<212> TYPE: DNA
<213> ORGANISM: Chlamydia trachomatis

<400> SEQUENCE: 40
gccaacactg ggactgagac actgcccaga ctcctacggg aggctgcagt    50

<210> SEQ ID NO 41
<211> LENGTH: 50
<212> TYPE: DNA
<213> ORGANISM: Mycoplasma pneumoniae

<400> SEQUENCE: 41
agccacaatg ggactgagac acggcccata ctcctacggg aggcagcagt    50

<210> SEQ ID NO 42
<211> LENGTH: 50
<212> TYPE: DNA
<213> ORGANISM: Bacteroides forsythus

<400> SEQUENCE: 42
gctaactccg tgccagcagc cgcggtaata cggaggatgc gagcgttatc    50

<210> SEQ ID NO 43
<211> LENGTH: 50

```
<212> TYPE: DNA
<213> ORGANISM: Porphyromonas gingivalis
<220> FEATURE:
<221> NAME/KEY: misc_feature
<222> LOCATION: 27, 36, 41
<223> OTHER INFORMATION: n = A,T,C or G

<400> SEQUENCE: 43
gctaactccg tgccagcagc cgcggtnata cggagnatgc nagcgttatc          50

<210> SEQ ID NO 44
<211> LENGTH: 50
<212> TYPE: DNA
<213> ORGANISM: Prevotella melaninogenica
<220> FEATURE:
<221> NAME/KEY: misc_feature
<222> LOCATION: 41
<223> OTHER INFORMATION: n = A,T,C or G

<400> SEQUENCE: 44
gctaattccg tgccagcagc cgcggtaata cggaaggtcc nggcgttatc          50

<210> SEQ ID NO 45
<211> LENGTH: 50
<212> TYPE: DNA
<213> ORGANISM: Cytophaga baltica

<400> SEQUENCE: 45
gctaactccg tgccagcagc cgcggtaata cggatggtcc gagcgttatc          50

<210> SEQ ID NO 46
<211> LENGTH: 50
<212> TYPE: DNA
<213> ORGANISM: Campylobacter jejuni
<220> FEATURE:
<221> NAME/KEY: misc_feature
<222> LOCATION: (0)...(0)
<223> OTHER INFORMATION: Also Helicobacter pylori.

<400> SEQUENCE: 46
gtgaactccg tgccagcagc cgcggtaata cggagggtgc aagcgttact          50

<210> SEQ ID NO 47
<211> LENGTH: 50
<212> TYPE: DNA
<213> ORGANISM: Treponema denticola
<220> FEATURE:
<221> NAME/KEY: misc_feature
<222> LOCATION: (0)...(0)
<223> OTHER INFORMATION: Also Treponema pallidum.

<400> SEQUENCE: 47
gctaattacg tgccagcagc cgcggtaaca cgtaaggggc gagcgttgtt          50

<210> SEQ ID NO 48
<211> LENGTH: 50
<212> TYPE: DNA
<213> ORGANISM: Leptothrix mobilis

<400> SEQUENCE: 48
gctaactacg tgccagcagc cgcggtaata cgtagggtgc aagcgttaat          50

<210> SEQ ID NO 49
<211> LENGTH: 50
<212> TYPE: DNA
<213> ORGANISM: Thiomicrospira denitrificans
<220> FEATURE:
```

```
<221> NAME/KEY: misc_feature
<222> LOCATION: (0)...(0)
<223> OTHER INFORMATION: Also Neisseria meningitidis.

<400> SEQUENCE: 49
gctaactacg tgccagcagc cgcggtaata cgtagggtgc gagcgttaat              50

<210> SEQ ID NO 50
<211> LENGTH: 50
<212> TYPE: DNA
<213> ORGANISM: Actinobacillus actinomycetemcomitans

<400> SEQUENCE: 50
gctaactccg tgccagcagc cgcggtaata cgggggggtgc gagcgttaat             50

<210> SEQ ID NO 51
<211> LENGTH: 50
<212> TYPE: DNA
<213> ORGANISM: Haemophilus influenzae

<400> SEQUENCE: 51
gctaactccg tgccagcagc cgcggtaata cggagggtgc gagcgttaat              50

<210> SEQ ID NO 52
<211> LENGTH: 50
<212> TYPE: DNA
<213> ORGANISM: Escherichia coli
<220> FEATURE:
<221> NAME/KEY: misc_feature
<222> LOCATION: (0)...(0)
<223> OTHER INFORMATION: Also Vibrio cholerae.

<400> SEQUENCE: 52
gctaactccg tgccagcagc cgcggtaata cggagggtgc aagcgttaat              50

<210> SEQ ID NO 53
<211> LENGTH: 50
<212> TYPE: DNA
<213> ORGANISM: Coxiella burnetii

<400> SEQUENCE: 53
gctaactccg tgccagcagc cgcggtaata cagagagtgc aagcgttaat              50

<210> SEQ ID NO 54
<211> LENGTH: 50
<212> TYPE: DNA
<213> ORGANISM: Legionella pneumophila

<400> SEQUENCE: 54
gctaactccg tgccagcagc cgcggtaata cggagggtgc gagcgttaat              50

<210> SEQ ID NO 55
<211> LENGTH: 50
<212> TYPE: DNA
<213> ORGANISM: Pseudomonas aeroginosa

<400> SEQUENCE: 55
gctaacttcg tgccagcagc cgcggtaata cgaagggtgc aagcgttaat              50

<210> SEQ ID NO 56
<211> LENGTH: 50
<212> TYPE: DNA
<213> ORGANISM: Caulobacter vibrioides
<220> FEATURE:
<221> NAME/KEY: misc_feature
```

-continued

```
<222> LOCATION: (0)...(0)
<223> OTHER INFORMATION: and Nitrobacter winogradskyi.

<400> SEQUENCE: 56
gctaacttcg tgccagcagc cgcggtaata cgaaggggc tagcgttgct          50

<210> SEQ ID NO 57
<211> LENGTH: 50
<212> TYPE: DNA
<213> ORGANISM: Rhodospirillum rubrum

<400> SEQUENCE: 57
gctaacttcg tgccagcagc cgcggtaata cgaaggggc aagcgttgtt          50

<210> SEQ ID NO 58
<211> LENGTH: 50
<212> TYPE: DNA
<213> ORGANISM: Wolbachia sp.

<400> SEQUENCE: 58
gctaactccg tgccagcagc cgcggtaata cggagagggc tagcgttatt          50

<210> SEQ ID NO 59
<211> LENGTH: 50
<212> TYPE: DNA
<213> ORGANISM: Myxococcus xanthus

<400> SEQUENCE: 59
gctaactctg tgccagcagc cgcggtaata cagagggtgc aagcgttgtt          50

<210> SEQ ID NO 60
<211> LENGTH: 50
<212> TYPE: DNA
<213> ORGANISM: Corynbacterium diphtheriae

<400> SEQUENCE: 60
gctaactacg tgccagcagc cgcggtaata cgtagggtgc gagcgttgtc          50

<210> SEQ ID NO 61
<211> LENGTH: 50
<212> TYPE: DNA
<213> ORGANISM: Mycobacterium tuberculosis

<400> SEQUENCE: 61
gccaactacg tgccagcagc cgcggtaata cgtagggtgc gagcgttgtc          50

<210> SEQ ID NO 62
<211> LENGTH: 50
<212> TYPE: DNA
<213> ORGANISM: Streptomyces coelicolor

<400> SEQUENCE: 62
gctaactacg tgccagcagc cgcggtaata cgtagggcgc aagcgttgtc          50

<210> SEQ ID NO 63
<211> LENGTH: 50
<212> TYPE: DNA
<213> ORGANISM: Actinomyces odontolyticus
<220> FEATURE:
<221> NAME/KEY: misc_feature
<222> LOCATION: 41
<223> OTHER INFORMATION: n = A,T,C or G

<400> SEQUENCE: 63
```
gctaactacg tgccagcagc cgcggtaata cgtagggcgc nagcgttgtc        50

<210> SEQ ID NO 64
<211> LENGTH: 50
<212> TYPE: DNA
<213> ORGANISM: Bacillus subtilis
<220> FEATURE:
<221> NAME/KEY: misc_feature
<222> LOCATION: (0)...(0)
<223> OTHER INFORMATION: Also Listeria monocytogenes, Enterococcus
      faecalis, Lactobacillus acidophilus, and
      Veillonella dispar.

<400> SEQUENCE: 64
gctaactacg tgccagcagc cgcggtaata cgtaggtggc aagcgttgtc        50

<210> SEQ ID NO 65
<211> LENGTH: 50
<212> TYPE: DNA
<213> ORGANISM: Staphylococcus aureus

<400> SEQUENCE: 65
gctaactacg tgccagcagc cgcggtaata cgtaggtggc aagcgttatc        50

<210> SEQ ID NO 66
<211> LENGTH: 50
<212> TYPE: DNA
<213> ORGANISM: Streptococcus mutans
<220> FEATURE:
<221> NAME/KEY: misc_feature
<222> LOCATION: 4, 41
<223> OTHER INFORMATION: n = A,T,C or G

<400> SEQUENCE: 66
gctnactacg tgccagcagc cgcggtaata cgtaggtccc nagcgttgtc        50

<210> SEQ ID NO 67
<211> LENGTH: 50
<212> TYPE: DNA
<213> ORGANISM: Clostridium botulinum

<400> SEQUENCE: 67
gctaactacg tgccagcagc cgcggtaata cgtaggtggc gagcgttgtc        50

<210> SEQ ID NO 68
<211> LENGTH: 50
<212> TYPE: DNA
<213> ORGANISM: Peptostreptococcus micros

<400> SEQUENCE: 68
gctaaatacg tgccagcagc cgcggtaata cgtatggggc gagcgttgtc        50

<210> SEQ ID NO 69
<211> LENGTH: 50
<212> TYPE: DNA
<213> ORGANISM: Fusobacterium nucleatum
<220> FEATURE:
<221> NAME/KEY: misc_feature
<222> LOCATION: 41
<223> OTHER INFORMATION: n = A,T,C or G

<400> SEQUENCE: 69
gctaaatacg tgccagcagc cgcggtaata cgtatgtcac nagcgttatc        50

<210> SEQ ID NO 70
<211> LENGTH: 50

<210> SEQ ID NO 70
<211> LENGTH: 50
<212> TYPE: DNA
<213> ORGANISM: Chlamydia trachomatis

<400> SEQUENCE: 70
gctaactccg tgccagcagc tgcggtaata cggagggtgc tagcgttaat          50

<210> SEQ ID NO 71
<211> LENGTH: 50
<212> TYPE: DNA
<213> ORGANISM: Mycoplasma pneumoniae

<400> SEQUENCE: 71
actaactatg tgccagcagt cgcggtaata cataggtcgc aagcgttatc          50

<210> SEQ ID NO 72
<211> LENGTH: 50
<212> TYPE: DNA
<213> ORGANISM: Bacteroides forsythus

<400> SEQUENCE: 72
acgaaagcgt gggtatcaaa caggattaga taccctggta gtccacgcag          50

<210> SEQ ID NO 73
<211> LENGTH: 50
<212> TYPE: DNA
<213> ORGANISM: Porphyromonas gingivalis

<400> SEQUENCE: 73
acgaaggcgt gggtatcaaa caggattaga taccctggta gtccacgcag          50

<210> SEQ ID NO 74
<211> LENGTH: 50
<212> TYPE: DNA
<213> ORGANISM: Prevotella melaninogenica

<400> SEQUENCE: 74
tcgaaggtgc gggtatcaaa caggattaga taccctggta gtccgcacag          50

<210> SEQ ID NO 75
<211> LENGTH: 50
<212> TYPE: DNA
<213> ORGANISM: Cytophaga baltica

<400> SEQUENCE: 75
acgaaagcgt gggtagcgaa caggattaga taccctggta gtccacgccg          50

<210> SEQ ID NO 76
<211> LENGTH: 50
<212> TYPE: DNA
<213> ORGANISM: Campylobacter jejuni
<220> FEATURE:
<221> NAME/KEY: misc_feature
<222> LOCATION: (0)...(0)
<223> OTHER INFORMATION: Helicobacter pylori also.

<400> SEQUENCE: 76
gcgaaagcgt ggggagcaaa caggattaga taccctggta gtccacgccc          50

<210> SEQ ID NO 77
<211> LENGTH: 50
<212> TYPE: DNA
<213> ORGANISM: Treponema denticola

<400> SEQUENCE: 77
acgaaggtgc ggggagcaaa caggattaga taccctggta gtccgcacag         50

<210> SEQ ID NO 78
<211> LENGTH: 50
<212> TYPE: DNA
<213> ORGANISM: Treponema pallidum

<400> SEQUENCE: 78
gcgaaggtgt ggggagcgaa caggattaga taccctggta gtccacacag         50

<210> SEQ ID NO 79
<211> LENGTH: 50
<212> TYPE: DNA
<213> ORGANISM: Leptothrix mobilis

<400> SEQUENCE: 79
acgaaagcgt ggggagcaaa caggattaga taccctggta gtccacgccc         50

<210> SEQ ID NO 80
<211> LENGTH: 50
<212> TYPE: DNA
<213> ORGANISM: Thiomicrospira denitrificans

<400> SEQUENCE: 80
acgaaagcgt gggtagcaaa caggattaga taccctggta gtccacgccc         50

<210> SEQ ID NO 81
<211> LENGTH: 50
<212> TYPE: DNA
<213> ORGANISM: Neisseria meningitidis

<400> SEQUENCE: 81
ccgaaagcgt gggtagcaaa caggattaga taccctggta gtccacgccc         50

<210> SEQ ID NO 82
<211> LENGTH: 50
<212> TYPE: DNA
<213> ORGANISM: Actinobacillus actinomycetemcomitans

<400> SEQUENCE: 82
gcgaaagcgt ggggagcaaa caggattaga taccctggta gtccacgctg         50

<210> SEQ ID NO 83
<211> LENGTH: 50
<212> TYPE: DNA
<213> ORGANISM: Haemophilus influenzae

<400> SEQUENCE: 83
gcgaaagcgt ggggagcaaa caggattaga taccctggta gtccacgctg         50

<210> SEQ ID NO 84
<211> LENGTH: 50
<212> TYPE: DNA
<213> ORGANISM: Escherichia coli

<400> SEQUENCE: 84
gcgaaagcgt ggggagcaaa caggattaga taccctggta gtccacgccg         50

<210> SEQ ID NO 85
<211> LENGTH: 50
<212> TYPE: DNA
<213> ORGANISM: Salmonella typhi
<220> FEATURE:
<221> NAME/KEY: misc_feature

```
<222> LOCATION: (0)...(0)
<223> OTHER INFORMATION: Also Vibrio cholerae, Pseudomonas aeruginosa,
      and Rhodospirillum rubrum.

<400> SEQUENCE: 85
gcgaaagcgt ggggagcaaa caggattaga taccctggta gtccacgccg            50

<210> SEQ ID NO 86
<211> LENGTH: 50
<212> TYPE: DNA
<213> ORGANISM: Coxiella burnetii

<400> SEQUENCE: 86
gcgaaagcgt ggggagcgaa caggattaga gaccctggta gtccacgccg            50

<210> SEQ ID NO 87
<211> LENGTH: 50
<212> TYPE: DNA
<213> ORGANISM: Legionella pneumophila

<400> SEQUENCE: 87
acgaaagcgt ggggagcaaa caggattaga taccctggta gtccacgctg            50

<210> SEQ ID NO 88
<211> LENGTH: 50
<212> TYPE: DNA
<213> ORGANISM: Caulobacter vibrioides

<400> SEQUENCE: 88
tcgaaagcgt ggggagcaaa caggattaga taccctggta gtccacgccg            50

<210> SEQ ID NO 89
<211> LENGTH: 50
<212> TYPE: DNA
<213> ORGANISM: Nitrobacter winogradskyi

<400> SEQUENCE: 89
acgaaagcgt ggggagcaaa caggattaga taccctggta gtccacgccg            50

<210> SEQ ID NO 90
<211> LENGTH: 50
<212> TYPE: DNA
<213> ORGANISM: Wolbachia sp.

<400> SEQUENCE: 90
gcgaaagcgt ggggagcaaa caggattaga taccctggta gtccacgctg            50

<210> SEQ ID NO 91
<211> LENGTH: 50
<212> TYPE: DNA
<213> ORGANISM: Myxococcus xanthus

<400> SEQUENCE: 91
gcgaaagcgt ggggagcaaa caggattaga taccctggta gtccacgccc            50

<210> SEQ ID NO 92
<211> LENGTH: 50
<212> TYPE: DNA
<213> ORGANISM: Corynebacterium diphtheriae

<400> SEQUENCE: 92
gcgaaagcat ggggagcgaa caggattaga taccctggta gtccatgccg            50
```

<210> SEQ ID NO 93
<211> LENGTH: 50
<212> TYPE: DNA
<213> ORGANISM: Mycobacterium tuberculosis

<400> SEQUENCE: 93
gcgaaagcgt ggggagcgaa caggattaga taccctggta gtccacgccg       50

<210> SEQ ID NO 94
<211> LENGTH: 50
<212> TYPE: DNA
<213> ORGANISM: Streptomyces coelicolor

<400> SEQUENCE: 94
gcgaaaggct ggggagcgaa caggattaga taccctggta gtccacgccg       50

<210> SEQ ID NO 95
<211> LENGTH: 50
<212> TYPE: DNA
<213> ORGANISM: Actinomyces odontolyticus

<400> SEQUENCE: 95
gcgaaagcgt ggggagcgaa caggattaga taccctggta gtccacgctg       50

<210> SEQ ID NO 96
<211> LENGTH: 50
<212> TYPE: DNA
<213> ORGANISM: Bacillus subtilis

<400> SEQUENCE: 96
gcgaaagcgt ggggagcgaa caggattaga taccctggta gtccacgccg       50

<210> SEQ ID NO 97
<211> LENGTH: 50
<212> TYPE: DNA
<213> ORGANISM: Staphylococcus aureus

<400> SEQUENCE: 97
gcgaaagcgt ggggatcaaa caggattaga taccctggta gtccacgccg       50

<210> SEQ ID NO 98
<211> LENGTH: 50
<212> TYPE: DNA
<213> ORGANISM: Listeria monocytogenes

<400> SEQUENCE: 98
gcgaaagcgt ggggagcaaa caggattaga taccctggta gtccacgccg       50

<210> SEQ ID NO 99
<211> LENGTH: 50
<212> TYPE: DNA
<213> ORGANISM: Enterococcus faecalis

<400> SEQUENCE: 99
tcgaaagcgt ggggagcaaa caggattaga taccctggta gtccacgccg       50

<210> SEQ ID NO 100
<211> LENGTH: 50
<212> TYPE: DNA
<213> ORGANISM: Lactobacillus acidophilus

<400> SEQUENCE: 100
tcgaaagcat ggtagcgaaa caggattaga taccctggta gtccatgccg       50

```
<210> SEQ ID NO 101
<211> LENGTH: 50
<212> TYPE: DNA
<213> ORGANISM: Streptococcus mutans
<220> FEATURE:
<221> NAME/KEY: misc_feature
<222> LOCATION: 37
<223> OTHER INFORMATION: n = A,T,C or G

<400> SEQUENCE: 101
tcgaaagcgt gggtagcgaa caggattaga taccctngta gtccacgccg         50

<210> SEQ ID NO 102
<211> LENGTH: 50
<212> TYPE: DNA
<213> ORGANISM: Clostridium botulinum
<220> FEATURE:
<221> NAME/KEY: misc_feature
<222> LOCATION: (0)...(0)
<223> OTHER INFORMATION: Also Peptostreptococcus micros.

<400> SEQUENCE: 102
acgaaagcgt gggtagcaaa caggattaga taccctggta gtccacgccg         50

<210> SEQ ID NO 103
<211> LENGTH: 50
<212> TYPE: DNA
<213> ORGANISM: Veillonella dispar

<400> SEQUENCE: 103
gcgaaagcca ggggagcgaa cgggattaga taccccggta gtcctggccg         50

<210> SEQ ID NO 104
<211> LENGTH: 50
<212> TYPE: DNA
<213> ORGANISM: Fusobacterium nucleatum

<400> SEQUENCE: 104
gcgaaagcgt gggtagcaaa caggattaga taccctggta gtccacgccg         50

<210> SEQ ID NO 105
<211> LENGTH: 50
<212> TYPE: DNA
<213> ORGANISM: Chlamydia trachomatis

<400> SEQUENCE: 105
gcgaaagcaa ggggagcaaa caggattaga taccctggta gtccttgccg         50

<210> SEQ ID NO 106
<211> LENGTH: 50
<212> TYPE: DNA
<213> ORGANISM: Mycoplasma pneumoniae

<400> SEQUENCE: 106
ttgaaagtgt ggggagcaaa taggattaga taccctagta gtccacaccg         50
```

METHOD OF DETECTING MICROORGANISMS

This is a U.S. National Phase under 35 U.S.C. §371 of International Application PCT/AU01/00933, filed Jul. 27, 2001, which claims priority to Australian Provisional Patent Application No. PQ9090, filed Jul. 28, 2000.

FIELD OF THE INVENTION

The present invention relates generally to a method for detecting, enumerating and/or identifying microorganisms in a sample. More particularly, the present invention provides a method for determining total microbial content in a sample by detecting the presence of nucleotide sequences associated with all or part of 16S rDNA or its corresponding 16S rRNA or its homologue, functional equivalent or derivative. The nucleotide sequences of the present invention may be used as an indicator of any microorganism and, hence, represents a universal target sequence which is indicative of total microbial content in a sample. The universal target sequence may also be varied to render same genus or species specific or the universal target used to trap microbial DNA or RNA which may be subsequently analyzed by sequence analysis or genetic probe technology. The universal target sequence is useful inter alia to design as universal primers and probes to amplify any microbial-derived genomic sequence, as a means to detect and enumerate total microorganisms and to identify microorganisms in a sample at the genus or species level. Such uses enable improved methods of enviroprotection, bioremediation, medical diagnosis and industrial microbiology. The present invention further relates to the universal target sequence in isolated form and/or primers or probes capable of hybridizing to same and kits for the detection of total microbial content in a sample.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

The rapidly increasing sophistication of DNA technology is greatly facilitating research and development in a range of disciplines including the medical and allied health industries, the agricultural and horticultural sectors and in the screening of related genomic sequences in environmental samples. Of particular importance is the application of molecular approaches to the characterization of bacterial communities. Such approaches overcome the limitations imposed by culture-mediated techniques for detecting microorganisms. It is known that the unculturable fraction of a microbial population represents a major component of all microbial communities (1, 2, 3).

Culture dependent methods for enumerating bacterial numbers are known to be biased since bacteria can only be cultivated if their metabolic and physiological requirements can be reproduced in vitro. These techniques may take several days to yield a result and, therefore, are inappropriate in situations where rapid diagnostic decisions are required. Where complex fastidious microbial communities are under investigation, such as the variety of microbial habitats in the oral cavity, enumerating bacteria by traditional microbial culturing techniques may also produce erroneous results.

Fluorescence-based methods for detecting bacteria can also be used to enumerate bacteria. For instance, flow cytometry can be applied to the rapid and automated counting of pure cultures used in industrial applications such as the food and biotechnology industries. However, most bacteria are optically too similar to resolve from each other or from debris using flow cytometry, without artificially modifying the target bacteria using fluorescent labelling techniques such as fluorescent antibodies or fluorescent dyes (4). The fluorescent DNA stain, diamidinopheylindole (5), for example, can be used to enumerate complex bacterial populations. However, differences in bacterial cell size, coaggregation of bacteria and the presence of different contaminating matrices (e.g. mud, food, dental plaque, dentine) can make meaningful counting difficult if not problematic as it can with direct or fluorescence microscopy (4).

Rapid enumeration of bacteria can also be achieved using a variety of molecular approaches (1, 2, 3, 6). Generally, however, multiple primers are required to detect the bacteria of interest. Techniques, such as competitive PCR (7, 8), are labour intensive and require the analysis of results from multiple reactions for each test sample. There is a need, therefore, to develop improved molecular approaches to microbial detection and enumeration.

Real-time PCR such as the TaqMan (Registered trade mark) system developed by Applied Biosystems relies on the release and detection of a fluorogenic probe during each round of DNA amplification. It allows for the rapid detection and quantification of DNA without the need for post-PCR processing such as gel electrophoresis and radioactive hybridization (9). In addition, the built-in 96 well format greatly increases the number of samples that can be simultaneously analyzed. The method uses the 5' exonuclease activity of a Taq polymerase (AmpliTaq Gold, PE Biosystems (Foster City, Calif., USA) during primer extension to cleave a dual-labelled, fluorogenic probe hybridized to the target DNA between the PCR primers. Prior to cleavage, a reporter dye, such as 6-carboxyfluorescein (6-FAM) at the 5' end of the probe is quenched by 6-carboxy-tetramethyl-rhodamine (TAMRA) through fluorescent resonance energy transfer. Following digestion, FAM is released. The resulting fluorescence is continuously measured in real-time at 518 nm during the log phase of product accumulation and is proportional to the number of copies of the target sequence.

In work leading up to the present invention, the inventors developed a set of oligonucleotides in the form of primers and probes which universally permit detection and quantification of the total bacterial load within a sample. The primers and probes are directed to 16S rDNA or its 16S rRNA and are conveniently used with real-time PCR or similar or related technology to detect and enumerate any microorganism not being a Eucarya or Archea. The development of a universal primer-probe set permits the rapid and accurate determination of microbial load without necessitating the development of specific primers for particular microorganisms. However, such specific primers may additionally be used to identify microorganisms at the genus or species level. The present invention further provides nucleic and extraction procedures useful inter alia in screening total biota for the presence of microorganisms.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention provides the design and evaluation of a set of universal primers and probes for the amplification of 16S rDNA or 16S rRNA from microorganisms to estimate total bacterial load by inter alia Real-Time PCR or similar or related technology. The universal primers and probes enable broad specificity in terms of the range of microorganisms which can be detected whilst not detecting Eucarya or Archea. A DNA standard representing those bacteria most likely to predominate in a given habitat is useful to more accurately determine total bacterial load. The universal primers and probes for total microbial-derived genomic material can be modified to enable identification and enumeration of microbial genera or species. Alternatively, or in addition, the universal primers/probes may be used as a trap for microbial 16S rDNA or 16S rRNA which may then be sequenced or interrogated by genus or species specific probes or primers. A nucleic acid extraction procedure is also provided in accordance with the present invention. The universal primers and probes have a range of uses in the medical, agricultural and other commercial industries.

Accordingly, one aspect of the present invention contemplates a method for determining total microbial content in a sample, said method comprising amplifying a target nucleotide sequence which is substantially conserved amongst two or more species of microorganisms, said amplification being for a time and under conditions sufficient to generate a level of an amplification product which is proportional to the level of microorganisms in said sample.

Another aspect of the present invention provides a method for determining total microbial content in a sample, said method comprising amplifying a target nucleotide sequence comprising or associated with 16S rDNA or 16S rRNA or a homologue or derivative or functional equivalent thereof, said amplification being for a time and under conditions sufficient to generate a level of an amplification product which is proportional to the level of microorganisms in said sample.

Yet another aspect of the present invention is directed to a method for determining total microbial content in a sample, said method comprising subjecting a nucleotide sequence defining or associated with 16S rDNA or 16S rRNA to Real-Time PCR or equivalent technology for a time and under conditions to generate a level of amplification product which is proportional to the level of microorganisms in said sample.

Still another aspect of the present invention provides a complex comprising forward and reverse primers hybridized to complementary strands of a target sequence comprising all or part of 16S rDNA or 16S rRNA or a homologue or derivative or functional equivalent thereof and an oligonucleotide probe labelled at its 5' end by a fluorogenic reporter molecule and at its 3' end by a molecule capable of quenching said fluorogenic molecule, said oligonucleotide probe hybridized to a portion of said 16S rDNA or 16S rRNA which is nested between said forward and reverse primers.

Even yet another aspect of the present invention contemplates a method for determining the total microbial content in a sample, said method comprising subjecting DNA in said sample to Real-Time PCR using a primers-probe set which comprises primers selected to amplify DNA comprising or associated with 16S rDNA or 16S rRNA or a homologue or derivative or functional equivalent thereof and a probe which hybridizes to a nucleotide sequence nested between said primers wherein said probe is labelled at its 5' end by a fluorogenic reporter molecule and at its 3' end by a molecule capable of quenching said fluorogenic molecule, said amplification being for a time and under conditions to generate a level of amplification product which is proportional to the level of microorganisms in said sample.

Still another aspect of the present invention provides a method for identifying a particular microorganism or prevalence of a particular genus or species of microorganism in a sample, said method comprising capturing DNA or RNA in said sample by primer(s) having a nucleotide sequence complementary to a nucleotide sequence within 16S rDNA or 16S rRNA and then subjecting said captured DNA or RNA to nucleotide sequencing and/or interrogation by a genus or species specific probe and then determining the microorganism by the particular sequence or pattern of probe interrogation.

Even still another aspect of the present invention is directed to a kit in compartmental form, said kit comprising a compartment adapted to contain one or more primers capable of participating in an amplification reaction of DNA comprising or associated with 16S rDNA or 16S rRNA, another compartment comprising a probe labelled at its 5' end by a fluorogenic reporter molecule and at its 3' end by a molecule capable of quenching said fluorogenic molecule and optionally another compartment adapted to contain reagents to conduct an amplification reaction and optionally a compartment adapted for extraction of nucleic acid from cells.

A further aspect of the present invention contemplates a method for extracting nucleic acid material from a sample comprising microbial cells, said method comprising subjecting a concentrated sample of said cells to enzymatic degradation and lysing said cells in the presence of SDS and then purifying said nucleic acid material.

Another aspect of the present invention further provides a method for extracting nucleic acid material from a sample comprising microbial cells, said method comprising subjecting a concentrated sample of said cells to pressure-mediated disruption, enzymatic degradation and then lysing said cells in the presence of SDS and then purifying said nucleic acid material.

Yet another aspect of the present invention contemplates a method for determining microorganisms in a sample, said method comprising:

optionally subjecting a concentrated sample of said cells to pressure-mediated disruption followed by enzymatic degradation and then lysing said cells in the presence of SDS and then purifying said nucleic acid material;

amplifying said nucleic acid material in the presence of forward and reverse primers capable of hybridizing to a conserved nucleotide sequence within 16S rDNA or 16S rRNA;

optionally detecting the presence of amplified product in the presence of a probe labelled with a reporter molecule and determining the total microbial content; and optionally isolating the amplified product and either sequencing the isolated product or subjecting the amplified product to genetic interrogation to identify the genus or species of microorganism present.

BRIEF DESCRIPTION OF THE FIGURES

FIG. 1 is a representation showing conservation of sequences used in the universal primer-probe set from the 16S rDNAs of bacteria representing most of the groups of Procarya defined in Bergey's Manual of Determinative Bacteriology (12). (A) Alignment of rDNAs showing conservation of 19 bp forward primer (outlined in bold). The bacterial sequences are designated SEQ ID NOS: 10-41. (B) Alignment of rDNAs showing conservation of 23 bp probe sequence (outlined in bold) The bacterial sequences are designated SEQ ID NOS: 42-71. (C) Alignment of rDNAs showing conservation of 26 bp reverse primer (outlined in bold). The bacterial sequences are designated SEQ ID NOS: 72-106.

DETAILED DESCRIPTION OF THE PREFERRED EMBODIMENTS

Figure 2:
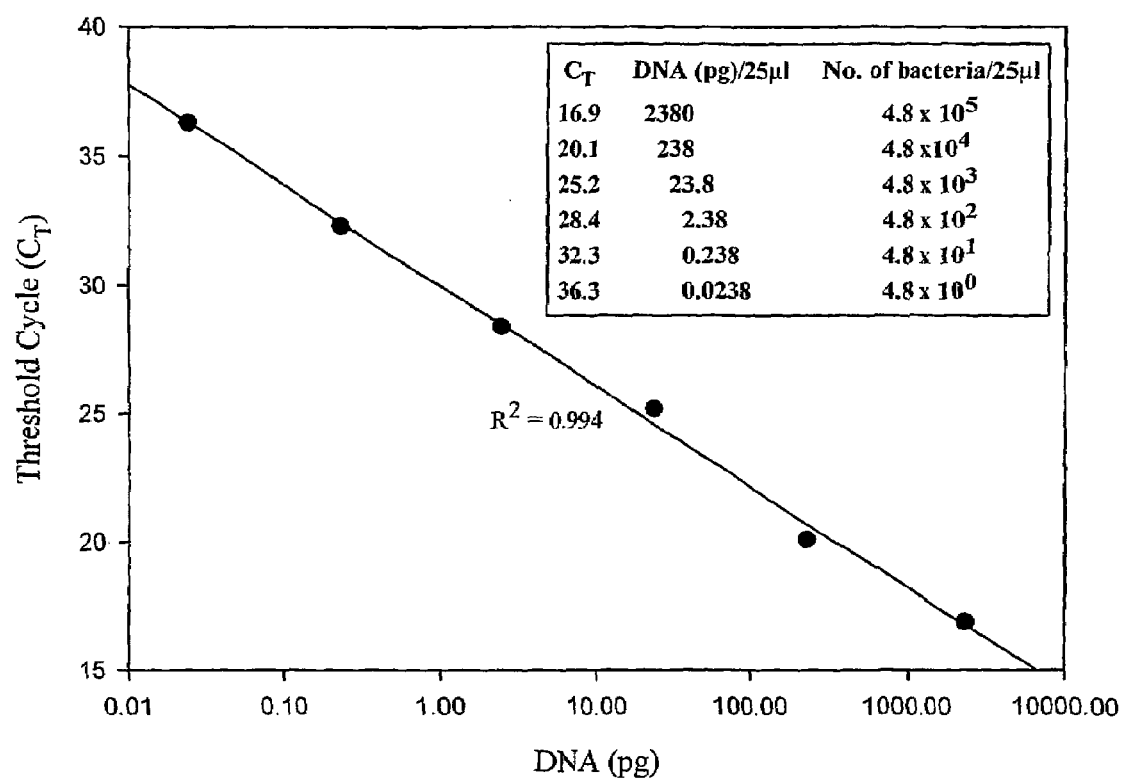
FIG. 2 is a graphical representation showing the standard curve using *E. coli* DNA.

The present invention is predicated in part on the identification of a nucleotide sequence associated with or comprising the 16S rDNA or 16S rRNA or its homologue, functional equivalent or derivative which is conserved amongst all prokaryotic microorganisms. The identification of these conserved nucleotide sequences enables the detection and quantification of total microbial content in a sample. The term "functional equivalent" in this context includes other conserved sequences which may also be used to determine total microbial content. The present invention provides primers and probes based on these conserved sequences which are "universal" in the sense that they are capable of hybridizing and/or amplifying microbial nucleic acid molecules without substantial cross reaction with DNA from Eucarya or Archea. The universal primers or probes may also be modified to render same genus or species specific or used in conjunction with other genus- or species-specific primers or probes such as to interrogate amplified nucleic acid material. The universal primers and probes may also be used as a "trap" for prokaryotic nucleic acid material which may inter alia be sequenced to assist in identifying a particular microorganism or to determine the prevalence of a particular microorganism at the genus or species level.

Accordingly, one aspect of the present invention contemplates a method for determining total microbial content in a sample, said method comprising amplifying a target nucleotide sequence which is substantially conserved amongst two or more species of microorganisms, said amplification being for a time and under conditions sufficient to generate a level of an amplification product which is proportional to the level of microorganisms in said sample.

Reference to "determining" microbial content includes estimating, quantifying, calculating or otherwise deriving a level of microbial content. The level of microbial content is generally referred to as the total microbial content and includes microorganisms which are capable of being cultured as well as microorganisms which cannot be cultured. The level of total microbial content is conveniently expressed in terms of number of microbial cells per particular volume, wet or dry weight of microbial cells per particular volume or other suitable indicator of the total number of cells in a sample. Conveniently, the number of cells is expressed per millilitre, per microlitre or per 25 or 50 microlitres. The number of microorganisms may also be determined indirectly such as corresponding to a particular amount of DNA. For example, 0.496 picogram of *E. coli* DNA corresponds to approximately 100 *E. coli* cells in the sample. The term "determining" may also be identifying a particular microorganism or ascertaining the prevalence of a particular microorganism at the genus or species level. This may, for example, be accomplished by nucleotide sequence and/or nucleic acid interrogation by species- or genus-specific probes.

The term "microorganism" is used in its broadest sense and includes Gram negative aerobic bacteria, Gram positive aerobic bacteria, Gram negative microaerophillic bacteria, Gram positive microaerophillic bacteria, Gram negative facultative anaerobic bacteria, Gram positive facultative anaerobic bacteria, Gram negative anaerobic bacteria, Gram positive anaerobic bacteria, Gram positive asporogenic bacteria and Actinomycetes. Conveniently, reference herein to a microorganism includes a member of the group of Procarya as listed in Bergey's Manual of Determinative Bacteriology (12). The term "microorganism" or "microbial" generally pertains to a bacterium or bacterial and which is not a member of Eucarya or Archea.

Although the present invention is particularly directed to those microorganisms listed in Table 3, the present invention extends to any microbial cell which carries the conserved target nucleotide sequence.

The term "sample" is used in its broadest sense to include biological, medical, agricultural, industrial and environmental samples. For example, samples may be derived from culture fluid, biopsy fluid or tissue from human, animal or insect sources, samples from natural environments such as soil, river, hot mineral water springs, plant, antarctic, air or extraterrestrial samples as well as samples from industrial sites such as waste sites and areas of oil spills or aromatic or complex molecule contamination and pesticide contamination. The sample may also comprise food, food components, food derivatives and/or food ingredients including food products formed in the dairy industry such as milk. The sample may be liquid, solid, slurry, air, vapour, droplet or aerosol or a combination of any of the above.

The target nucleotide sequence is generally a target DNA or RNA sequence. If the target is an RNA sequence, then this sequence may have to be subject to reverse transcription to generate a complementary DNA sequence (cDNA). Conveniently, the target nucleotide sequence is DNA and is conserved amongst two or more species of microorganisms. In a particularly preferred embodiment, the target sequence is ribosomal DNA (rDNA) such as but not limited to 16S rDNA or is ribosomal RNA (rRNA) such as but not limited to 16S rRNA. With respect to the latter, suitable microbial cells are any cells which comprise a conserved sequence comprising or associated with 16S rDNA or 16S rRNA. Reference herein to "16S rDNA" or "16S rRNA" includes reference to any homologues or derivatives thereof as well as functional equivalents thereof A "homologue" of 16S rDNA includes RNA forms such as 16S rRNA or vice versa.

Accordingly, a preferred aspect of the present invention provides a method for determining total microbial content in a sample, said method comprising amplifying a target nucleotide sequence comprising or associated with 16S rDNA or 16S rRNA or a homologue or derivative or functional equivalent thereof, said amplification being for a time and under conditions sufficient to generate a level of an amplification product which is proportional to the level of microorganisms in said sample.

Although the present invention may be practised directly on single stranded template from a non-amplified nucleic acid molecule, in a preferred embodiment the template nucleic acid molecule is from a nucleic acid molecule which has been subjected to amplification. Any of a range of amplification reactions may be employed including PCR, rolling circle amplification and Qβ replicase based amplification amongst others.

The preferred amplification conditions are those which result in real-time Real-Time PCR. The amplification product is then measured to a particular amount referred to herein as the threshold concentration ($C_T$). The $C_T$ is proportional to the total target sequence (e.g. 16S rDNA) and hence proportional to total bacterial content. Generally a standard curve is prepared based on the $C_T$ and known amounts of DNA in pg by determining the level of amplification product under conditions giving a $C_T$, this then determines the amount of microbial target sequence and, hence, microbial levels. The use of Real-Time PCR is preferred but the present invention permits the use of related technology.

Accordingly, another aspect of the present invention is directed to a method for determining total microbial content in a sample, said method comprising subjecting a nucleotide sequence defining or associated with 16S rDNA or 16S rRNA or a homologue or derivative or functional equivalent thereof to Real-Time PCR for a time and under conditions to generate a level of amplification product which is proportional to the level of microorganisms in said sample.

Preferably, the level of amplification product is defined by $C_T$.

The time and conditions for amplification such as Real-Time PCR is such that, in a preferred embodiment, $C_T$ is recorded. These conditions are the same as for preparation of a standard curve.

In a particularly preferred embodiment, the amplification is conducted with a set of primers (forward and reverse) and a probe oligonucleotide labelled with a fluorogenic reporter molecule at its 5' end and a quenching molecule at its 3' end. The quenching molecule prevents emission of signal from the fluorogenic reporter molecule. The probe oligonucleotide hybridizes to a region of the target sequence between the regions to which the forward and reverse primers hybridize. As the polymerase moves along the strand to which the probe oligonucleotide has hybridized, the 5' end of the probe is cleaved off by the exonuclease activity of the polymerase thus permitting emission of the fluorogenic signal due to separation of the quenching moiety.

In another embodiment, therefore, the present invention provides a complex comprising forward and reverse primers hybridized to complementary strands of a target sequence comprising all or part of 16S rDNA or 16S rRNA or a homologue or derivative or functional equivalent thereof and an oligonucleotide probe labelled at its 5' end by a fluorogenic reporter molecule and at its 3' end by a molecule capable of quenching said fluorogenic molecule, said oligonucleotide probe hybridized to a portion of said 16S rDNA which is nested between said forward and reverse primers.

The preferred primers and probes of the present invention exhibit at least one of the following properties:
(i) comprise a melting temperature ($T_m$) of DNA between about 58° C. and about 60° C. for primers and about 68° C. and 70° C. for the probe;
(ii) comprise a GC content of between about 30 and 80%;
(iii) comprise no more than three consecutive G's in the primer or probe;
(iv) comprise no more than 2 GC's in the last 5 nucleotides at the 3' end of the primer;
(v) comprise no G on the 5' end of the probe;
(vi) the selection of probe should be from the strand with more C's than G's; and
(vii) the amplicon length should be between about 50 and about 150 bp.

In a most preferred embodiment, primers-probe set are as follows:

```
Universal forward primer:
TCCTACGGGAGGCAGGAGT                    (SEQ ID NO:1)

Universal reverse primer:
GGACTACCAGGGTATCTAATCCTGTT             (SEQ ID NO:2)
```

```
-continued
Universal probe:
CGTATTACCGCGGCTGCTGGCAC.            (SEQ ID NO:3)
```

Accordingly, another aspect of the present invention contemplates a method for determining the total microbial content in a sample, said method comprising subjecting DNA in said sample to Real-Time PCR using a primers-probe set which comprise primers selected to amplify DNA comprising or associated with 16S rDNA or 16S rRNA or a homologue or derivative or functional equivalent thereof and a probe which hybridizes to a nucleotide sequence nested between said primers wherein said probe is labelled at its 5' end by a fluorogenic reporter molecule and at its 3' end by a molecule capable of quenching said fluorogenic molecule, said amplification being for a time and under conditions to generate a level of amplification product which is proportional to the level of microorganisms in said sample.

Preferably, the forward and reverse primers and probe are those defined by SEQ ID NO:SEQ ID NO:1, SEQ ID NO:2 and SEQ ID NO:3, respectively or forward and reverse primers and probe which hybridize to a complementary form of SEQ ED NO:1, SEQ ID NO:2 or SEQ ID NO:3, respectively under low stringency conditions and/or which exhibit at least about 70% similarity to SEQ ID NO:1, SEQ ID NO:2 or SEQ ID NO:3 or their complementary forms. The probe is conveniently labelled at its 5' end with a reporter molecule such as but not limited to a fluorescent dye, for example, 6-carboxyfluorescein (6-FAM). The 3' end is conveniently labelled with a quenching molecule such as but not limited to 6-carboxy-tetramethylrhodamine (TAMRA).

The term "similarity" as used herein includes exact identity between compared sequences at the nucleotide level. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous nucleotides that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (18). A detailed discussion of sequence analysis can be found in Unit 19.3 of Ausubel et al. (19).

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by, for example, GAP in the Wisconsin Genetics Software Package or other programs such as the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at least from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m = 69.3 + 0.41$ (G+C) % (20). However, the $T_m$ of a duplex DNA decreases by 1° C. with every increase of 1% in the number of mismatch base pairs (21). Formamide is optional in these hybridization conditions. Accordingly, particularly preferred levels of stringency are defined as follows: low stringency is 6×(SSC) buffer, 0.1% w/v sodium dodecyl sulphate (SDS) at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The primers and probes may be modified to render same genus- or species-specific. Alternatively, or in addition, further primers or probes may be employed to specifically define a genus or species of microorganism by, for example, primer/probe interrogation. With respect to the former, the universal primer/probe set may be used as a trap for 16S rDNA/rRNA or its homologues, equivalents or derivatives which is then subjected to identification of genus or species of the microorganism or of the predominant microorganism. Some partial preselection may also be conducted to bias the sample to, for example, particular types of microorganisms such as aerobes, anaerobes or microbes having particular nutritional requirements or features or antibiotic-resistance microbes.

Accordingly, another aspect of the present invention contemplates a method for identifying a particular microorganism or prevalence of a particular genus or species of microorganism in a sample, said method comprising capturing DNA or RNA in said sample to primer having a nucleotide sequence complementary to a nucleotide sequence within 16S rDNA or 16S rRNA and then subjecting said captured DNA or RNA to nucleotide sequencing and/or interrogation by a genus or species specific probe and then determining the microorganism by the particular sequence or pattern of probe interrogation.

In a related embodiment, there is provided a method for identifying a microorganism by its genus in a sample, said method comprising subjecting DNA in said sample to Real-Time PCR using a primers-probe set which comprises primers selected to amplify DNA comprising or associated with 16S rDNA or 16S rRNA and a probe which hybridizes to a nucleotide sequence nested between said primers wherein said probe is either specific for said microorganism to be identified or which is subsequently identified by a genus-specific probe.

In a preferred embodiment, the primer is also a genus-specific probe.

In one particularly useful embodiment, the primer/probe set is used to trap nucleic acid material which is then cloned and sequenced to determine the genus or species of the predominant microbe. A decision may then be made to study or cultivate the predominant microbe. This is particularly useful in the study of anaerobic bacteria which have fastidious culture requirements which make then difficult to culture. This is even more particularly useful for isolating and identifying anaerobic bacteria from dental plaques which are difficult to culture using conventional procedures. DNA or RNA may be extracted, subjected to PCR by the universal primers and then the amplified fragment isolated and sequenced and the organism identified by BLAST/GAP or other computer analysis.

Reference herein to a "primer" or "probe" is not to be taken as any limitation as to structure, size or function. The primer may be used as an amplification molecule or may be used as a probe for hybridization purposes. The preferred form of the molecule is as a primer for amplification.

Reference herein to a "nucleic acid primer" includes reference to a sequence of deoxyribonucleotides or ribonucleotides comprising at least 3 nucleotides. Generally, the nucleic acid primer comprises from about 3 to about 100 nucleotides, preferably from about 5 to about 50 nucleotides and even more preferably from about 5 to about 25 nucleotides. A primer having less than 50 nucleotides may also be referred to herein as an "oligonucleotide primer". The primers of the present invention may be synthetically produced by, for example, the stepwise addition of nucleotides or may be fragments, parts, portions or extension products of other nucleotide acid molecules. The term "primer" is used in its most general sense to include any length of nucleotides which, when used for amplification purposes, can provide a free 3' hydroxyl group for the initiation of DNA synthesis by a DNA polymerase. DNA synthesis results in the extension of the primer to produce a primer extension product complementary to the nucleic acid strand to which the primer has hybridized. The primer or probe may also be considered as a trapping or anchoring moiety from the target DNA or RNA.

The extension of the hybridized primer to produce an extension product is included herein by the term "amplification". Amplification generally occurs in cycles of denaturation followed by primer hybridization and extension. The present invention encompasses from about 1 cycle to about 120 cycles, preferably from about 2 to about 70 cycles and even more preferably from about 5 to about 40 cycles including about 10, 15, 20, 25 and 30 cycles.

In a particularly preferred embodiment, preparation of the sample is conducted in the presence of a nuclease inhibitor.

The assay may be conducted in any of a number of forms. In one example, an immobilized form of the assay is contemplated. In one embodiment, a generic primer is immobilized to a solid support to capture target DNA/RNA. Solution phase forward and reverse primers and the probe are then used to perform the Real-Time PCR or by related or equivalent technology. In an alternative embodiment, one of the forward or reverse primers is used as the capture molecule.

In accordance with this aspect of the present invention, a sample of nucleic acid to be tested for the presence of bacteria is added to a chamber, well or other receptacle comprising an immobilized nucleic acid capture molecule. The capture molecules comprise a nucleotide sequence substantially complementary to a portion of either the target nucleotide sequence or a nucleotide sequence within a nucleic acid molecule comprising the target sequence. The terms "captive molecule" and "primer" may be used interchangedly.

The capture molecule may be immobilized to the solid phase by any convenient means. The solid phase may be any structure having a surface which can be derivatized to anchor a nucleic acid primer or other capture molecule. Preferably, the solid phase is a planar material such as the side of a microtitre well or the side of a dipstick.

The anchored nucleic acid molecule generally needs to be able to capture a target nucleic acid molecule by hybridization and optionally participate in an amplification reaction. Alternatively, the anchored nucleic acid molecule will capture amplified nucleic acid molecules.

Methods for linking nucleic acid molecules to solid supports are well known in the art. Processes for linking the primer to the solid phase include amide linkage, amidate linkage, thioether linkage and the introduction of amino groups on to the solid phase. Examples of linkage to a solid phase can be found in International Patent Application No. PCT/AU92/00587 [WO 93/09250].

The anchored primer may also participate with one of the solution phase primers for amplification. Alternatively, a "generic" primer is anchored to the solid support in order to amplify the nucleic acid molecule comprising a target sequence. Specific amplification of the target sequence can then be achieved by solution phase primers. In relation to the latter embodiment, the solution would contain two solution phase primers and a labelled probe.

Anchored primers may also be used to trap target DNA or RNA for subsequent cloning and/or sequencing (generally after amplification) and/or interrogation by probes or primers to identify a genus or species of microorganism or the predominant microorganism.

The method of the present invention provides an efficient, cost effective and accurate means of detecting particular nucleic acid molecules and thereby quantitating bacterial load.

As stated above, the universal primers and probes of the present invention are also useful as a trap for total microbial-derived target material. Such trapped material may then be sequenced, or cloned and sequenced and/or subjected to primer/probe interrogation. Consequently, the present invention provides an ability to detect bacteria from samples which are difficult to cultivate and that would in all practicality remain undetected or under-estimated by viable culture count methods or, alternatively, bacteria that are in an aggregated or coaggregated state or contaminated with matrix material, such as in carious dentine samples, where fluorescent detection and/or microscopic enumeration are also impractical. In addition, the application of the universal primers and probes of the present invention enable rapid differentiation of bacteria from viral infections within the limited time constraints sometimes experienced in life-threatening clinical situations. This is particularly useful, for example, in assessing encephalitis and distinguishing between microbial and viral encephalitis. In the field of clinical microbiology, the present invention enables the trapping and identification of, the predominate bacterium in an infection which leads to more efficacious treatment protocols. Any and all applications of the subject method are encompassed by the present invention.

The present invention is applicable to a range of industries including the medical, agricultural and industrial industries with specific uses including enviroprotection, bioremediation, medical diagnosis, water quality control or food quality control.

Yet another aspect of the present invention is directed to a kit in compartmental form, said kit comprising a compartment adapted to contain one or more primers capable of participating in an amplification reaction of DNA comprising or associated with 16S rDNA or 16S rRNA, another compartment comprising a probe labelled at its 5' end by a fluorogenic reporter molecule and at its 3' end by a molecule capable of quenching said fluorogenic molecule and optionally another compartment adapted to contain reagents to conduct an amplification reaction and optionally a compartment adapted for extraction of nucleic acid from cells.

In an alternative embodiment, the kit comprises a microtitre tray with two or more wells and with the reagents including the primers in the wells.

One or more of the primers may also be immobilized to the compartments.

The kit may conveniently be adapted for automated or semi-automated use.

The kit may also comprise a compartment for nucleic acid extraction.

The kit may also comprise an array of primers or probes to permit detection of not only total Procarya but also other microorganisms or specific bacteria.

The present invention further provides an extraction procedure for extracting nucleic acid material for amplification by the universal primer/probe set.

Accordingly, the present invention contemplates a method for extracting nucleic acid material from a sample comprising microbial cells, said method comprising subjecting a concentrated sample of said cells to enzymatic degradation and lysing said cells in the presence of SDS and then purifying said nucleic acid material.

Preferably, the enzymatic treatment comprises treatment with a proteinase K and lysozyme and/or mutanolysin or their equivalents. Preferably, the lysed cells are also treated with an RNase. Conveniently, DNA or RNA is then specifically isolated.

This method is referred to as a single step DEPC method.

A two-step DEPC method is further contemplated by the present invention and this could include a pressure-mediated cell lysis step (such as by sonication) or incubation on ice, in the presence of DEPC prior to enzymatic treatment.

Accordingly, the present invention further provides a method for extracting nucleic acid material from a sample comprising microbial cells, said method comprising subjecting a concentrated sample of said cells to pressure-mediated disruption, or incubation on ice, in the presence of DEPC prior to enzymatic degradation and then lysing said cells in the presence of SDS and then purifying said nucleic acid material.

Preferably, the pressure-mediated disruption is sonication. The other preferred aspects of this two-step method are the same as the one-step method.

In a particular preferred embodiment, the one- or two-step extraction methods are used in combination with the universal primers/probe set to enumerate and optionally identify particular bacteria in a sample.

Accordingly, the present invention contemplates a method for determining microorganisms in a sample, said method comprising:

optionally subjecting a concentrated sample of said cells to pressure-mediated disruption or incubation on ice, in the presence of DEPC followed by enzymatic degradation and then lysing said cells in the presence of SDS and then purifing said nucleic acid material;

amplifying said nucleic acid material in the presence of forward and reverse primers capable of hybridizing to a conserved nucleotide sequence within 16S rDNA or 16S rRNA;

optionally detecting the presence of amplified product in the presence of a probe labelled with a reporter molecule and determining the total microbial content; and optionally isolating the amplified product and either sequencing the isolated product or subjecting the amplified product to genetic interrogation to identify the genus or species of microorganism present.

The present invention is further described by the following non-limiting Examples.

EXAMPLE 1

Bacterial Strains and Culture Conditions

*Escherichia coli* strains JM109, NM522 and XL 1 blue (Stratagene, La Jolla, Calif., USA) were available from previous studies. *Staphylococcus aureus* strains ATCC 12600, ATCC 9144, ATCC 12598, ATCC BM 10458 and ATCC BM 1014; *Staphylococcus epidemidis* strains ATCC 35983 and ATCC 14990; *Staphylococcus hemolyticus* ATCC 29970 and *S. hemolyticus*-infiltrative keratitis isolate; *Staphylococcus schleferi* ATCC 43808; *Pseudomonas aeurginosa* strains ATCC 19660, ATCC 15442, ATCC 6294 and ATCC 6206; *Pseudomonas fluorescens*-infiltrative keratitis isolate; *Pseudomonas putida*-lens saline isolate; *Pseudomonas stutzeri*-infiltrate isolate; *Pseudomonas alcaligens* laboratory-isolate; *Pseudomonas* species and *Serratia marcescens* ATCC 274 were provided by the Co-operative Research Centre for Eye Research and Technology, The University of New South Wales, Australia. All *Escherichia*, *Staphylococcus*, *Pseudomonas* and *Serratia* species were grown in Luria Burtanni broth at 37° C. *Streptococcus mutans* LT 11 and *Streptococcus sanguis* ATCC 10556 were grown at 37° C. on Brain Heart Infusion broth (Oxoid, Basingstoke, UK) under 95% $N_2$/5% v/v $CO_2$; *Fusobacterium nucleatum* ATCC 25586, *Fusobacterium necrophorum* ATCC 25286, *Actinomyces israelii* ATCC 12102 and *Actinomyces naeslundii* ATCC 12104 were obtained from the American Type Culture Collection (Rockville, Md., USA) and grown at 37° C. in a Brain Heart Infusion broth in an anaerobic chamber (85% v/v $N_2$, 5% v/v $CO_2$, 10% v/v $H_2$). *Porphyromonas gingivalis* ATCC 33277, *Prevotella melaninogenica* ATCC 25845, *Prevotella loescheii* ATCC 15930, *Peptostreptococcus micros* ATCC 33270 and *Peptostreptococcus anaerobius* ATCC 27337 were obtained from the American Type Culture Collection (Rockville, Md., USA) and grown at 37° C. on CDC broth (1% v/v trypticase peptone, DIFCO Becton Dickinson, Md., USA; 1% v/v trypticase soy broth, DIFCO Becton Dickinson, Md., USA; 0.5% w/v sodium chloride, 1% w/v yeast extract, Oxoid, Basingstoke, UK; 0.04% w/v L-cysteine, Sigma Chemical Co., St Louis, Mo., USA) containing 1% w/v hemin, 0.4% w/v menadione and 2% v/v horse serum in an anaerobic chamber (85% v/v $N_2$, 5% v/v $CO_2$, 10% v/v $H_2$). *Porphyromonas endodontalis* ATCC 35406 American Type Culture Collection (Rockville, Md., USA) was also grown in an anaerobic chamber. *Lactobacillus acidophilus* ATCC 4356 and *Lactobacillus rhamnosus* ATCC 7469 from the IDR culture collection were grown at 37° C. in MRS broth (Oxoid, Basingstoke, UK) under microaerophilic conditions (95% v/v $N_2$, 5% v/v $CO_2$).

EXAMPLE 2

Source of Carious Dentine

Twenty carious teeth were obtained with informed consent from randomly selected patients who presented with pain and requested extraction to relieve their symptoms. Patients were excluded from the study if they reported a history of significant medical disease or anti-microbial therapy within the previous four months. Unrestored teeth with coronal enamel and dentine caries were selected for inclusion in the study on the basis of clinical diagnostic tests which indicated that they were vital, with clinical symptoms of reversible pulpitis (pain and heightened sensitivity to hot and cold stimuli).

Immediately after extraction, each tooth was placed in a container of reduced transport fluid (RTF) (24) and transferred to an anaerobic chamber at 37° C. containing 85% $N_2$, 5% $CO_2$ and 10% $H_2$ v/v/v. Superficial plaque and debris overlying the carious lesion was removed and the surface rinsed several times with RTF. Using sterile sharp excavators, all the softened and carious dentine was collected as small fragments from each tooth. Sampling was completed within 20 min of tooth extraction.

EXAMPLE 3

Determination of Colony-forming Units in Carious Dentine

The carious dentine extracted from each tooth was individually weighed and a standard suspension of 10 mg wet wt dentine (ml RTF)$^{-1}$ was prepared at 37° C. in an anaerobic chamber (see Example 2). The dentine fragments were homogeneously dispersed in RTF by first vortexing for 20 s and then by homogenizing by hand in a 2 ml glass homogenizer for 30 s. Samples (100 µl) of $10^{-3}$ to $10^{-6}$ serial dilutions of these suspensions were prepared in RTF and plated in duplicate onto Trypticase Soy agar (Oxoid) containing 1 µg menadione ml$^{-1}$, 5 µg haemin ml$^{-1}$, 400 µg L-cysteine ml$^{-1}$ (Sigma) and 5% v/v horse blood (Amyl Media) (10). The plates were incubated at 37° C. in an anaerobic chamber containing 85% $N_2$, 5% $CO_2$ and 10% $H_2$ v/v/v for 14 days and the number of colony-forming units counted to determine the total microbial load (mg wet wt of dentine)$^{-1}$. The unused dispersed carious dentine samples were frozen at −80° C.

EXAMPLE 4

Determination of Viable Bacteria from In Vitro Cultures

Viable cell counts of cultures of *E. coli*, *P. aeruginosa* and *S. aureus* were determined by plating 100 µl of a $10^{-6}$ dilution of the appropriate culture grown in LB broth on LB agar plates and counting the colonies after aerobic incubation at 37° C. for 24 h.

EXAMPLE 5

Extraction of DNA from Bacterial Cultures

DNA was isolated from individual bacterial species using either the QIAamp DNA. Mini kit (QIAGEN, Clifton Hill, VIC) according to the manufacturer's instructions or using the freeze-boil method. In the latter instance, bacterial cells from a 250 µl of culture were obtained by centrifugation (14,000×g for 2 min at room temperature) and resuspended in 45 µl 10 mM phosphate buffer pH 6.7 prior to freezing at −20° C. The frozen cells were then heated in a boiling water bath for 10 min.

EXAMPLE 6

Extraction of Anaerobic Bacterial DNA from Carious Dentine

Frozen suspensions of homogenized carious dentine were thawed on ice and 80 µl samples removed and combined with 100 µl ATL buffer (Qiagen) and 400 µg proteinase K (Qiagen). The samples were vortexed for 10 s and then incubated at 56° C. for 40 min with periodic vortexing for 10 s every 10 min to allow complete lysis of the cells. This procedure was found to extract DNA from both Gram-negative and Gram-positive anaerobic bacteria in line with the finding that the cell-wall integrity of Gram-positive anaerobes is compromised when the bacteria are exposed to oxygen (11). Other micro-aerophilic or facultative Gram-positive bacteria including streptococci, lactobacilli and Actinomyces were not lysed by this procedure. Following the addition of 200 µg RNase (Sigma), the samples were incubated for a further 10 min at 37° C. DNA free of contaminating RNA was then purified using the QIAmp DNA Mini Kit (Qiagen) according to the manufacturer's instructions.

EXAMPLE 7

Sources of Other Bacterial DNA

DNA from *Legionella pneumophila* serogroup 4 ATCC 33156, serogroup 5 ATCC 33216, serogroup 6 ATCC 33215, serogroup 1 Knoxyille-1 ATCC 33153, philadephia-1 as well as *Legionella anisa*, *Legionella bozenianii* serogroup-2, *Legionella londineenisis*, *Legionella maceachernii* and *Legionella waltersii* were provided by The Infectious Diseases Laboratories, Institute of Medical and Veterinary Science, South Australia; and those from *Mycobacterium tuber-* culosis H37RV by The Microbiology Laboratory, Westmead Hospital, New South Wales, Australia.

EXAMPLE 8

DNA Sequence Analysis

The 16S rDNA sequences representing most of the Groups of bacteria outlined in Bergey's Manual (registered trade mark) of Determinative Bacteriology (12) that were analyzed for construction of a universal primers-probe set included (GenBank Accession Number in parentheses) *Bacteroides forsythus* (AB035460), *P. gingivalis* (POYRR16SC), *P. melaninogenica* (PVORR16SF), *Cytophaga baltica* (CBA5972), *Campylobacter jejuni* (CAJRRDAD), *Helicobacter pylon* (HPU00679), *Treponema denticola* (AF139203), *T. pallidum* (TRPRG16S), *Leptothrix mobilis* (LM16SRR), *Thiomicrospira denitrificans* (TDE243144), *Neisseria meningitidis* (AF059671), *Actinobacillus actinomycetemcomitans* (ACNRRNAJ), *Haemophilus influenzae* (HIDNA5483), *E. coli* (ECAT1177T), *Salmonella typhi* (STRNA16), *Vibrio cholerae* (VC16SRRNA), *Coxiella burnetii* (D89791), *L. pneumophila* (LP16SRNA), *P. aeruginosa* (PARN16S), *Caulobacter vibrioides* (CVI009957), *Rhodospirillum rubrum* (RR16S107R), *Nitrobacter winogradskyi* (NIT16SRA), *Wolbachia* species (WSP010275), *Myxococcus xanthus* (MXA233930), *Corynebacterium diphtheriae* (CD16SRDNA), *M. tuberculosis* (MTRRNOP), *Streptomyces coelicolor* (SC16SRNA), *A. odontolyticus* (AO16SRD), *Bacillus subtilis* (AB016721), *S. aureus* (SA16SRRN), *Listeria monocytogenes* (S55472), *Enterococcus faecalis* (AB012212), *L. acidophilus* (LBARR16SAZ), *S. mutans* (SM16SRNA), *Clostridium botulinum* (CBA16S), *P. micros* (PEP16SRR8), *Veillonella dispar* (VDRRNA16S), *F. nucleatum* (X55401), *Chlamydia trachomatis* (D89067) and *Mycoplasma pneumoniae* (AF132741). The 16S rDNA sequences were aligned using the GCG program Pileup (22) accessed through the Australian National Genomic Information Service (ANGIS, http://www.angis.org.au). Regions of identity were assessed manually for the design of the universal probe and primers (FIGS. 1A, 1B, 1C) and then checked for possible cross hybridization with other bacterial genes using the database similarity search program BLAST (23), also accessed through ANGIS. The Primer Express Software provided by Applied Biosystems to determine the appropriate primer/probe combinations was of limited value in this exercise and was only used to check for primer-dimer or internal hairpin configurations. Once designed, the probe and primer sequences (Table 1) were synthesized by Applied Biosystems.

EXAMPLE 9

PCR Conditions

Amplification and detection of DNA by Real-Time PCR was performed with the ABI-PRISM 7700 Sequence Detection System (PE Biosystems, Foster City, Calif., USA) using optical grade 96 well plates. For determination of the predominantly anaerobic Gram negative bacterial load in carious dentine, the PCR reaction was carried out in triplicates in a total volume of 25 µl using either the TaqMan (registered trade mark) PCR Core Reagent Kit, PE Biosystems (Foster City, Calif., USA) to which was added 200 µM of each dNTP, 3.5 mM $MgCl_2$, 0.625 U AmpliTaq Gold in 1×PCR buffer supplied by PE Biosystems (Foster City, Calif., USA) using 300 nM forward and reverse primers and 175 nM fluorogenic probe. Alternatively, the TaqMan (registered trade mark) Universal PCR Master Mix (PE Biosystems, Foster City, Calif., USA) was used containing 100 nM of each of the universal forward and reverse primers and the fluorogenic probe. The reaction conditions for amplification of DNA were 50° C. for 2 min, 95° C. for 10 min and 40 cycles of 95° C. for 15 s and 60° C. for 1 min. Data were analyzed using the Sequence Detection System Software from PE Biosystems (Foster City, Calif., USA) and are presented as the mean of duplicate samples.

EXAMPLE 10

DNA Isolation Procedures (i) Sonication: Bacterial cells pelleted at 14,000×g for 2 min at room temperature were resuspended in 10 mM phosphate buffer pH 6.7 containing glass beads and were sonicated for 5 min, 10 min and 15 min, with 75 watts output using a Branson sonifier model 250. Aliquots were collected at each time interval.

(ii) Freeze-thaw method: The cell pellet was resuspended in 10 mM phosphate buffer pH 6.7, frozen at −20° C., and after thawing, an aliquot was used for the PCR reaction.

(iii) Freeze-boil method: Bacterial cells pelleted at 14,000×g for 2 min at room temperature were resuspended in 10 mM phosphate buffer pH 6.7, frozen at −20° C. and placed in boiling water for 10 min before using for the PCR reaction.

(iv) Enzymatic method: Bacterial cells pelleted at 14,000×g for 2 min at room temperature were resuspended in 10 mM phosphate buffer pH 6.7 containing lysozyme and mutanolysin (each with 1 mg/ml final concentration) and incubated at 60° C. for 30 min and lysed with SDS (1% w/v final concentration).

(v) QIAmp DNA Mini kit method: Total cell DNA was extracted from bacterial cultures with the QIAmp DNA Mini kit (QIAGEN) as per the manufacturer's instructions.

(vi) $ZnCl_2$/EDTA/DEPC method: Bacterial cells' pelleted at 14,000×g for 2 min at room temperature were resuspended in 10 mM phosphate buffer pH 6.7 containing lysozyme and mutanolysin (each with 1 mg/ml-final concentration) and 5 mM $ZnCl_2$ or 100 mM EDTA or 20 mM DEPC. After incubation at 60° C. for 30 min, the cells were lysed with 1% w/v SDS (final concentration). DNA was purified from bacterial cultures with the QIAmp DNA Mini kit as per the manufacturer's instructions.

EXAMPLE 11

Protection from Nucleases

Purified preparation of DNA and *P. gingivalis* cell extract were incubated at 60° C. for 30 min in the presence or absence of $ZnCl_2$ (5 mM) or EDTA (100 mM) or DEPC (20 mM) or rabbit muscle actin (1 µg/ml) or dipyridyl (2 mM/5 mM), to assess their effect as nuclease inhibitors. An aliquot was checked on 1% w/v agarose gel electrophoresis.

EXAMPLE 12

Design of Universal Primers and Probe

Applied Biosystems has set a number of guidelines for the design of primers and probes. These include the fact that the melting temperature ($T_m$) of the DNA should be between 58-60° C. for the primers and 68-70° C. for the probe; the G+C content should be between 30-80%; there should be no runs of more than three consecutive G's in either the primers or the probe; there should be no more than two GC's in the last five nucleotides at the 3' end of the primers; there should be no G on the 5' end of the probe; the selection of the probe should be from the strand with more C's than G's and the amplicon length should be between 50-150 bp.

The inventors then designed a set of universal primers and a probe based on the sequence of 16S rDNA which would substantially comply with at least most of the guidelines set by Applied Biosystems and also detect a broad range of bacterial species. In the inventors' hands, it was not possible to meet all of these criteria. The inventors' final choice for a universal primers-probe set, however, only deviated in two ways from the ideal. These were the length of the amplicon and the number of GC's in the last five nucleotides of the forward primer. The primers-probe set designed to act as a universal detection system for the Procarya by Real-Time PCR generated a 466 bp amplicon spanning residues 331 to 797 on the E. coli 16S rRNA gene (Table 1). The selected probe and primer sequences were highly conserved in all groups of Procarya (12) for which representative bacterial 16S rRNA genes were aligned (FIG. 1).

Although the multiple alignment of the selected bacterial 16S rRNA sequences show two mismatches in the forward primer of F. nucleatum (where the nucleotides are unknown) as well as a deletion in the 5' end of the forward primer of P. micros, these discrepancies were tolerated during Real-Time PCR since both genera could be quantified using the universal primers-probe set (Table 2).

To confirm the specificity for Procarya, the inventors searched a number of available Eucarya and Archea databases available through ANGIS. The BLAST search results showed only one significant hit—that of a specific breast cancer cell line (BT029) detected only by the reverse primer. However, the human DNA sample supplied by Applied Biosystems in their beta-actin detection kit was not amplified by the primers-probe set and gave a totally negative result.

EXAMPLE 13

Sensitivity of the Universal Primers-probe Set in Detecting E. coli rDNA

Figure 3:
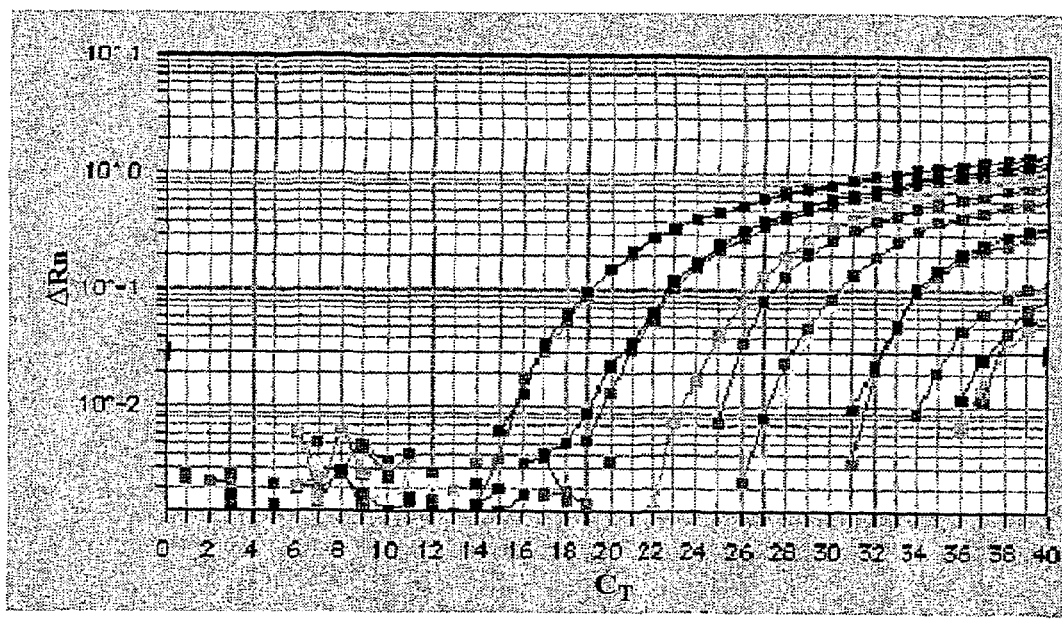
FIG. 3 is a graphical representation showing the sensitivity of the universal probe and primers in detecting *E. coli* DNA using Real-Time PCR. Purified *E. coli* DNA was used as the template in quantities 2380 pg, 238 pg, 23.8 pg, 2.38 pg, 238 fg, 23.8 fg, representing $C_T$ (threshold cycle) values in the range 16.9 to 36.3 where the intercept of the magnitude of the fluorescent signal ($\Delta R_n$) with the horizontal threshold line in bold represents the $C_T$ value for a given sample. The fluorescent signal at $C_T$ 37.7 corresponds to the no-template-control and represents bacterial DNA contamination in the commercially supplied reagents.

TaqMan (registered trade mark) technology determines the PCR cycle at which the increase in fluorescence of the reporter dye reaches a threshold. This is known as the threshold cycle ($C_T$) and is proportional to the amount of target DNA and hence the number of bacteria in the sample. The inventors produced a standard graph based on the detection of E. coli rDNA, where one E. coli cell theoretically equates to the detection of 4.96 fg DNA (FIG. 2). Using E. coli as a standard, between 238 fg of E. coli DNA (corresponding to 48 E. coli cells) and 2.38 ng of E. coli DNA (corresponding to $4.8 \times 10^5$ E. coli cells) was consistently detected. However, this does not take into consideration the number of rDNA copies on the E. coli genome. The limitation on the lower detection limit (i.e. between 4.8 cells to 48 cells) varied with the use of the TaqMan (registered trade mark) PCR Core Reagent Kit or the TaqMan (registered trade mark) Universal PCR Master Mix supplied by PE Biosystems (Foster City, Calif., USA). This is believed to be due to bacterial DNA contamination either in the enzyme preparation or in the chemical reagents used for PCR (13-16), an observation verified in this study by detection using the universal primer-probe set of rDNA in reagent mixes and negative controls containing no added E. coli DNA (FIG. 3). Although 40 PCR cycles are available with the universal primers-probe set, in the no-template-control, the fluorescent signal was consistently detected around a $C_T$ of 33 and 38

EXAMPLE 14

Broad Range Detection and Relative Determination of Bacterial Number

In order to determine the relative total bacterial load for a given species, the inventors compared the $C_T$ value for the test sample with a standard graph derived from known amounts of E. coli DNA (FIG. 2). The standard graph was preferably prepared from data accumulated at the same time as the test samples in order to act as an internal control. By using the standard curve, both the relative concentration of DNA in the sample and the relative number of bacteria could be determined for all selected species that represent the major Groups of bacteria listed in Bergey's Manual (registered trade mark) of Determinative Bacteriology (12) [Table 2]. For each of these species, there was little variance in the value of $2.00 \times 10^2$ (range $1.98-2.06 \times 10^2$) bacteria per pg DNA when E. coli DNA was used as a standard. This indicated that the source of DNA was not influencing the level of detection and that the primers-probe set was equally efficient in detecting the DNA irrespective of the species from which it was extracted. Similar conclusions could be drawn when different strains of the same species were detected by Real-Time PCR (Table 3).

EXAMPLE 15

Effect of the Source of Standard DNA on the measurement of Relative DNA Concentration Comparison with a DNA standard other than that of E. coli should result in a difference in the relative amount of DNA detected due to variations in rDNA copy number as well as the multiplying effect that the generation time ($t_d$) may have on this number. To confirm this, a comparison was made between the three rapidly growing aerobic bacteria, S. aureus, E. coli and P. aeruginosa, with $t_d$ in vitro in the order of 20-50 min and two slow growing obligate oral anaerobes, P. melaninogenica and P. endodontalis, with $t_d$ in vitro in the order of 5-15 h. The relative amount of DNA estimated by Real-Time PCR using each of the 5 DNAs as standards was related to the amount of DNA determined at $A_{260}$ nm (set at 100%). In each instance, it would be expected that comparison of like DNA by Real-Time PCR with the known amount of added DNA would be approximately 100%. In two instances this was not the case. For both P. aeruginosa and P. melaninogenica approximately twice the amount of DNA was detected. This was due in part to the fact that the relative amounts of DNA were calculated by the Sequence Detection System Version 1.6.3 software supplied by Applied Biosystems based upon the arbitrary placement of the horizontal threshold line used to determine the $C_T$ (as seen in FIG. 3). The horizontal threshold line was therefore adjusted to bring these two values as close to 100% as possible and the relative amount of DNA recalculated (Table 4).

As expected, variation in the relative amount of DNA was observed when the standard DNA differed from that of the species being evaluated (Table 4). However, significant error (>3-fold) was only observed when the fast growing aerobic bacteria were compared with the DNA standards of the slow growing obligate anaerobes (over estimation) or conversely, when the obligate anaerobes were compared to the DNA of the fast growing aerobes (under estimation) (Table 4).

One of the values, that of the amount of S. aureus DNA detected using the P. melaninogenica DNA, was approximately two-fold greater than expected. However, this value was calculated from a low $C_T$ value where significant error can arise due to the logarithmic scale of the abscissa in the graph of $C_T$ vs (DNA). At extreme high and low $C_T$ values, a two-fold error in the estimation of the relative amount of DNA can occur. By taking this inherent two-fold error into account and by subsequently altering one of the 25 values for the relative amount of DNA by a factor of two (Table 4—see footnote ‡), the data in Table 4 allowed an estimation of the ratio of the number of copies of the 16S rRNA operons in the different species. An average ratio of 23:13:10:2:1 (to the nearest integer) for the copy numbers in S. aureus, E. coli, P. aeruginosa, P. endodontalis and P. melaninogenica respectively fitted the modified data. This implied that the fast growing aerobes, S. aureus, E. coli and P. aeruginosa possessed approximately twice the known chromosomal complement of 16S rRNA operons. The data also predicted that the obligate anaerobes possess only one or two 16S rRNA operons per chromosome. The exact copy numbers are currently unknown.

EXAMPLE 16

Comparison of Viable Cell Numbers and the Relative Estimation of Bacteria in an Artificial In Vitro Mixture using Real-Time PCR In order to determine the validity of using the universal primers-probe set to estimate the total number of bacteria in a mixed culture, the three bacteria, E. coli, P. aeruginosa and S. aureus, were grown separately in vitro to stationary phase and equal volumes of the three cultures (2 ml) mixed together. The number of E. coli, P. aeruginosa and S. aureus colony forming units at stationary phase were determined by serial dilution on agar plates and compared with the relative bacterial load determined by Real-Time PCR using the universal primers-probe set and E. coli DNA as the standard. A consensus was noted in the estimation of bacterial counts irrespective of the method used (Table 5), despite the fact that the number of copies of the 16S rRNA operons in a single chromosome of E. coli is 7 while that in P. aeruginosa is 4 and S. aureus is 9, and the expectation that P. aeruginosa would be under-estimated and S. aureus over-estimated against the E. coli standard DNA.

EXAMPLE 17

Comparison of the Number of Anaerobic Bacteria in Carious Dentine by Real-Time PCR with the Total Anaerobic Colony Count The value of using the universal probe and primers set in estimating the anaerobic bacterial load in carious dentine was determined in twenty clinical samples using P. melaninogenica ATCC 25845 DNA from anaerobically grown cells as the standard. Comparison was made with the total anaerobic colony count for each of the samples. The mean number of anaerobic bacteria determined by Real-Time PCR was $3.6 \times 10^8$ (mg dentine)$^{-1}$ (range $1.1 \times 10^8$-$1.1 \times 10^9$ [mg dentine]$^{-1}$), while that for the total viable cell count was $1.1 \times 10^7$ (mg dentine)$^{-1}$ (range $2.0 \times 10^6$-$3.7 \times 10^7$ [mg dentine]$^{-1}$). The results indicated that the culture-based technique underestimated the total bacterial load in carious dentine, since the number of anaerobic bacteria that were detected in the samples by Real-Time PCR was, on average, 40-fold greater than that detected by colony counts despite the fact that the latter also contained facultative Gram-positive bacteria (Table 6).

EXAMPLE 18

Sonication of Bacterial Cells for Isolation of Bacterial DNA

Figure 4:
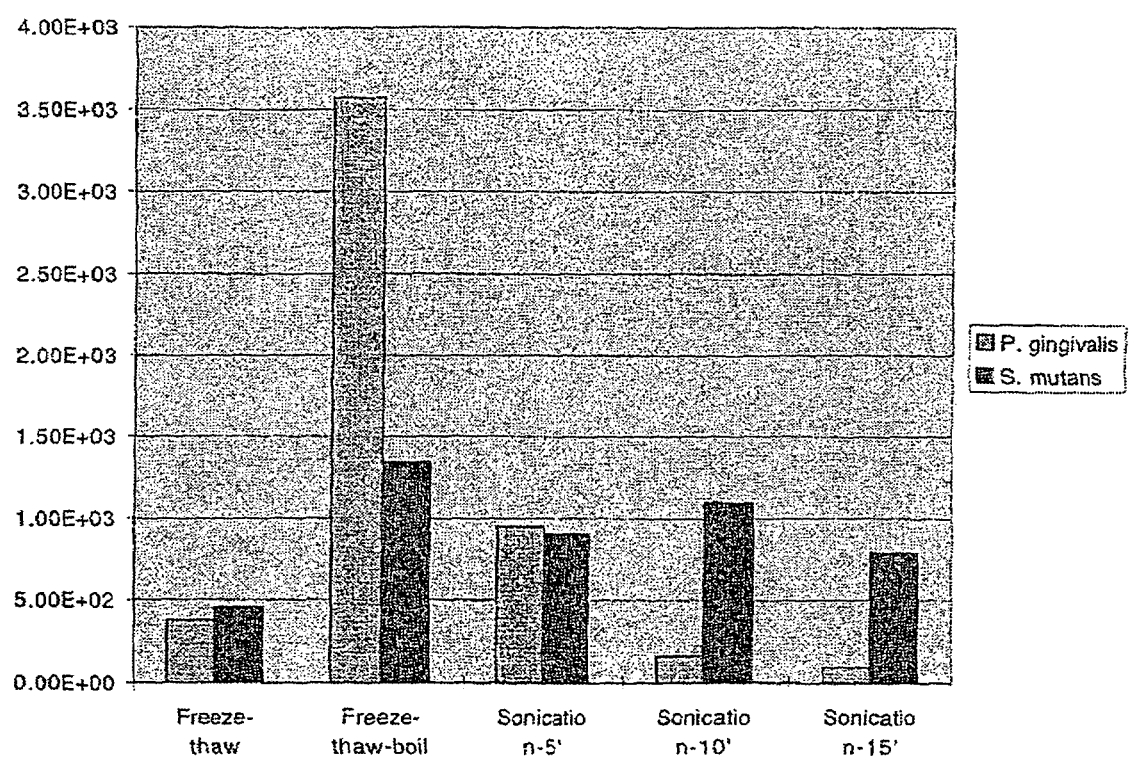
FIG. 4 is a graphical representation showing the effect of sonication of bacterial cells on the isolation of DNA.

To eliminate loss of DNA using a multistep sample preparation protocol, bacterial cell suspensions were sonicated to release DNA from cells for quantification using Real-Time PCR. DNA was released more effectively when the cells were sonicated using glass beads. Sonicates of S. mutans and P. gingivalis were diluted to the appropriate concentration and checked in the ABI-PRISM 7700 Sequence Detection System for quantification of DNA using the universal primers-probe set. The effect of sonication was compared with DNA isolation using freeze-thaw or freeze-boil. As seen in FIG. 4, the freeze-boil technique method released most DNA. Increased sonication times had little effect on DNA recovery from S. mutans, but had a negative effect on P. gingivalis recovery

EXAMPLE 19

Presence of Nucleases in P. Gingivalis as Seen on Agarose Gel Electrophoresis

Figure 5A:
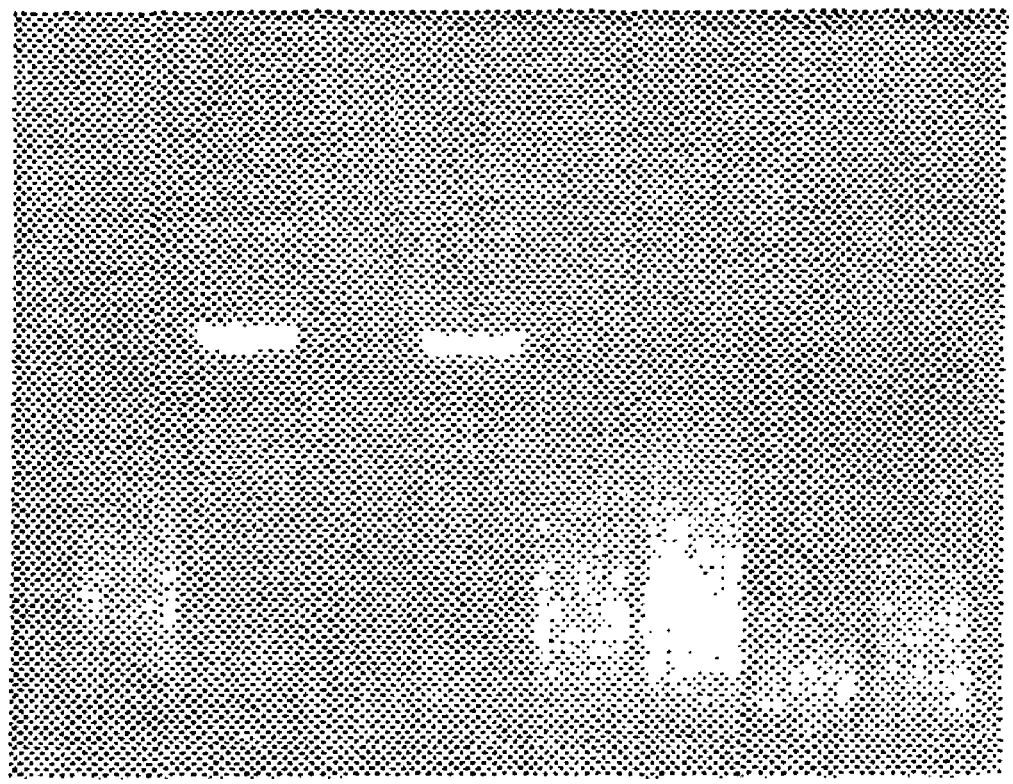
FIG. 5A is a photographic representation showing the presence of nucleases in *P. gingivalis*. (1) Freeze/thawed sample; (2) Freeze/thawed-boiled sample; (3) Freeze/thawed sample treated with mutanolysin; (4) Freeze/thawed-boiled sample treated with mutanolysin; (5) Sample sonicated for 3 min; (6) Sample sonicated for 6 min; (7) Sample sonicated for 3 min and treated with mutanolysin; and (8) Sample sonicated for 6 min and treated with mutanolysin.

The presence of nucleases in P. gingivalis was checked using 1% w/v agarose gel electrophoresis. Exogenous, purified, P. gingivalis DNA was incubated at 50° C. for 30 min with each of the DNA isolation fractions shown in FIG. 5A and when loaded on a 1% w/v agarose gel, intact DNA could be detected only after boiling the frozen culture, as seen in FIG. 5A.

EXAMPLE 20

Figure 6A:
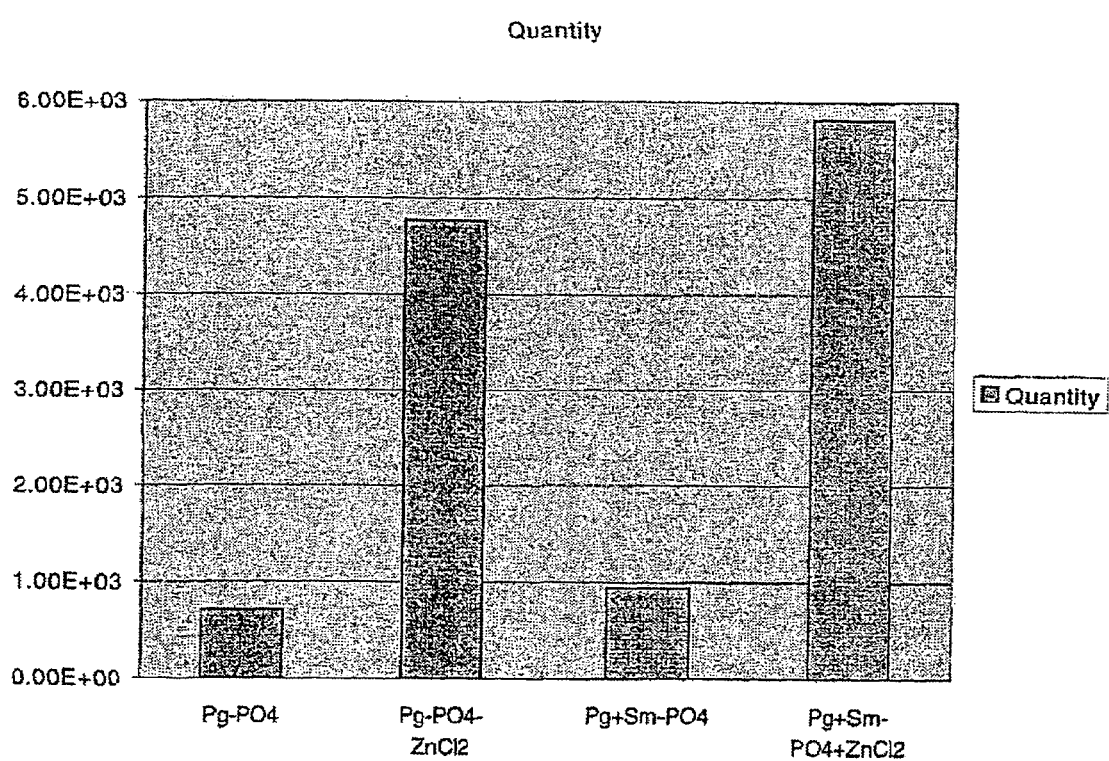
FIG. 6A is a graphical representation showing the critical role of nucleases and the effect of $ZnCl_2$ on the quantification of *P. gingivalis* and *P. gingivalis*+*S. mutans*.
Figure 6B:
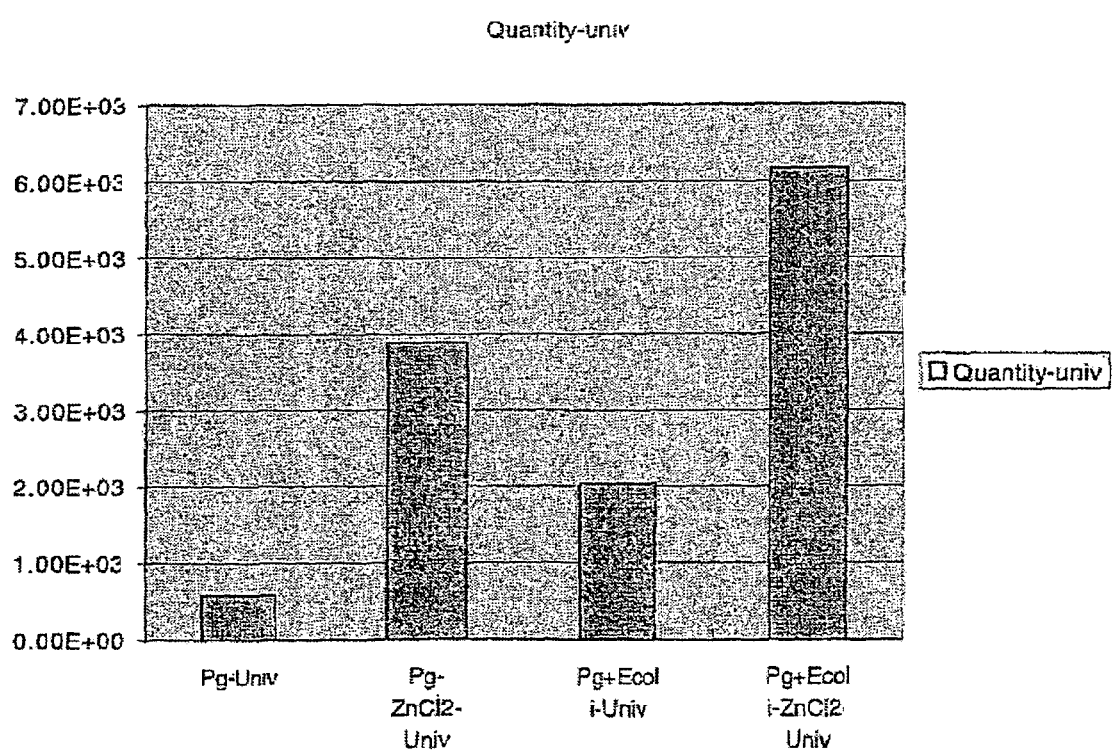
FIG. 6B is a graphical representation showing the critical role of nucleases and the effect of $ZnCl_2$ on the quantification of *P. gingivalis* and *P. gingivalis*+*E. coli*.

The Critical Role of Nucleases and the Effect of $ZnCl_2$ on the Quantification in Individual and Mixed Bacterial Populations DNA isolated from P. gingivalis, in the absence or presence of E. coli or S. mutans was checked in the ABI-PRISM 7700 Sequence Detection System, for quantification of DNA, using the universal primers-probe set and appropriate dilution of the sample. A significant increase in quantification of DNA was evident in individual and mixed bacterial populations in the presence of 5 mM $ZnCl_2$ (FIGS. 6a, 6b).

EXAMPLE 21

Effect of Removal of $ZnCl_2$ and SDS on Quantification Using Undiluted Samples

Figure 7:
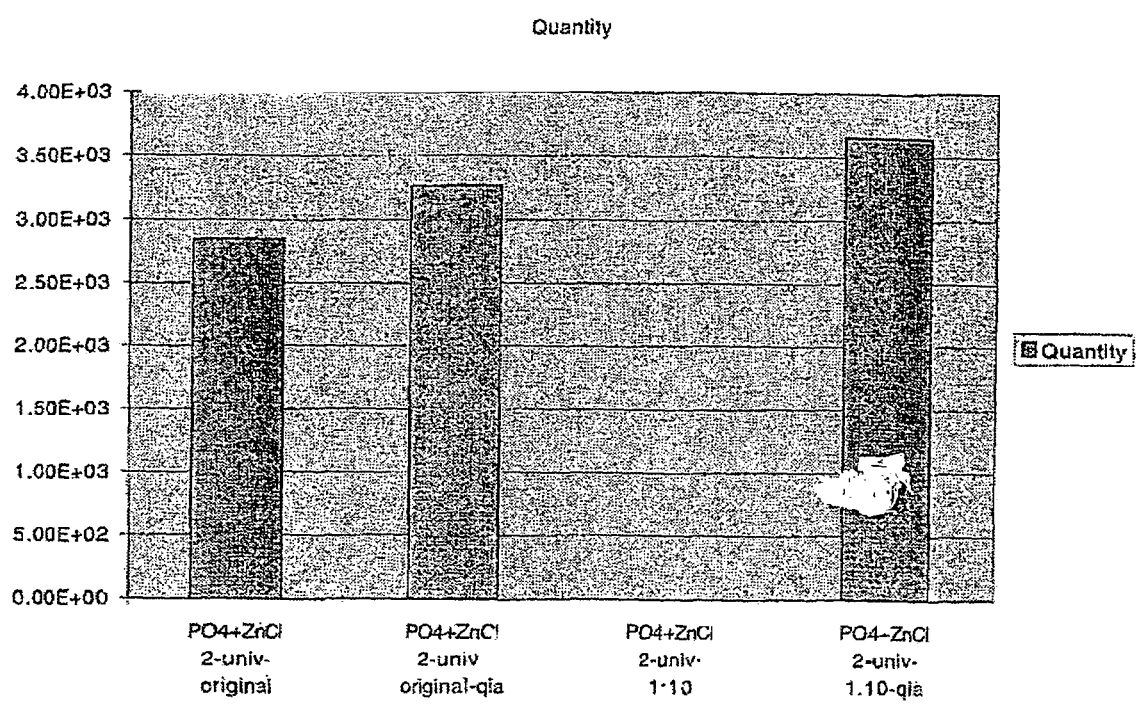
FIG. 7 is a graphical representation showing the effect of removal of $ZnCl_2$ and sodium dodecyl sulphate (SDS) on the quantification of DNA using undiluted samples.

To eliminate the interference of $ZnCl_2$ and SDS in undiluted or lower dilution samples, it was necessary to remove the nuclease inhibitor and cell lysis agent, respectively, before the DNA samples were analyzed in the ABI-PRISM 7700 Sequence Detection System. A P. gingivalis cell pellet, resuspended in 10 mM phosphate buffer pH 6.7, containing lysozyme and mutanolysin (each with 1 mg/ml-final concentration) and 5 mM $ZnCl_2$ was incubated at 60° C. for 30 min and then lysed with 1% w/v SDS, before purification of DNA using the QIAamp DNA Mini kit. Quantification of DNA could not be done in undiluted samples. This was possibly due to high concentrations of $ZnCl_2$ in the undiluted samples that could interfere with the PCR reaction. Purification of DNA using the QIAamp Mini kit restored the amount of DNA quantified as seen in FIG. 7.

EXAMPLE 22

Internal Positive Control Using B. tryoni dsX Gene Insert in pGEM (Registered Trade Mark)-T Easy Vector System A TaqMan (registered trade mark) exogenous, internal positive control was designed to be used with the ABI PRISM 7700 Sequence Detection System to determine the efficiency of DNA recovery following sample preparation and to evaluate the effect of any PCR inhibitors in the reaction. The forward primer 5'GGAAGGTAAGTTG-CATTTCAGCA3' [SEQ ID NO: 4], reverse primer 5'GCG-TACTTATCATGGTAAATTAAGTCAATT3' [SEQ ID NO:5] and fluorogenic probe, VIC-TCCCGTTA-CAAAATCGTGTTTACATCGTATACTCG [SEQ ID NO:6] were designed from the reported sequence of the dsX gene of Bactrocerra tryoni (GenBank Accession No. AF040077) using Primer Express software (Applied Biosystems, Foster City, Calif., USA). The probe sequence for this Internal Positive Control (IPC-BT-PG) was labelled with the fluorescent dye VIC at the 5' end to differentiate the IPC from the species specific and universal probes which are labelled with the fluorescent dye FAM at the 5' end.

Figure 8:
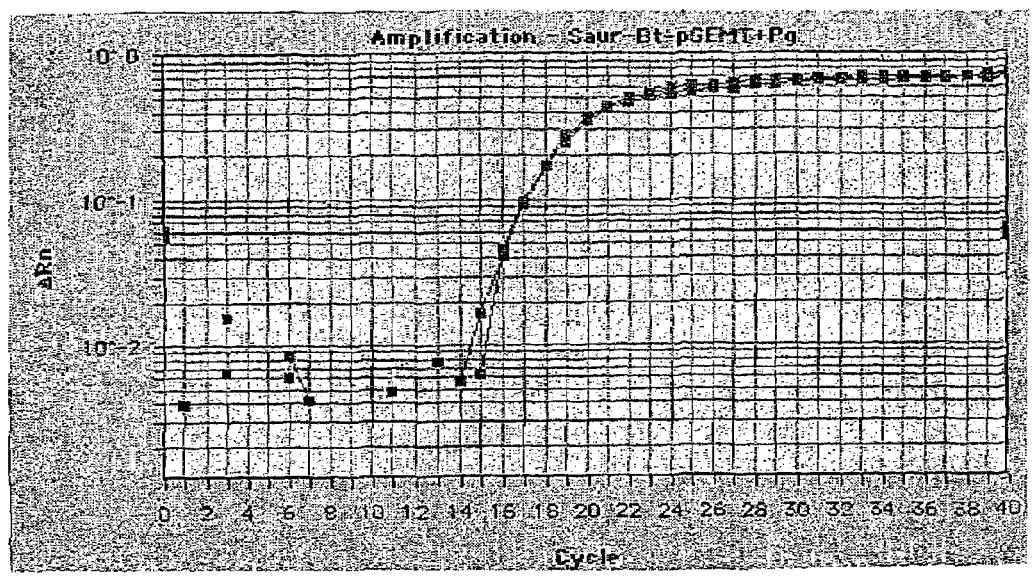
FIG. 8 is a graphical representation showing the internal positive control using *B. tryoni* dsX gene insert in pGEM (registered trade mark)-T Easy vector system.

B. tryoni dsX gene insert in pGEM (registered trade mark)-T Easy was confirmed by PCR and generated an 89 bp amplicon as seen on 2% w/v agarose gel electrophoresis. The chimeric plasmid also gave a fluorescent signal in the ABI-PRISM 7700 Sequence Detection System, confirming an internal site of the probe in the amplicon (FIG. 8).

EXAMPLE 23

Isolation of P. gingivalis DNA in the presence of the internal positive control

The P. gingivalis cell pellet (from 250 µl culture, spun at 14,000×g for 2 min at room temperature) was resuspended in 10 mM phosphate buffer pH 6.7 containing lysozyme and mutanolysin (each with 1 mg/ml-final concentration), 5 mM $ZnCl_2$ and the internal positive control (B. tryoni dsX gene insert in pGEM (registered trade mark)-T Easy Vector System) and was incubated at 60° C. for 30 min and then lysed with 1% w/v SDS. The same amount of culture pellet was also resuspended in 10 mM phosphate buffer pH 6.7 containing the internal positive control and kept frozen at −20° C. The frozen sample was boiled for 10 min. After diluting the sample, an aliquot was checked in the ABI-PRISM 7700 Sequence Detection System. A higher amount of DNA (lower $C_T$ value) was estimated for P. gingivalis and the internal positive control when the samples were either boiled or isolated in phosphate buffer containing 5 mM $ZnCl_2$ (as seen in Table 7), whereas P. gingivalis DNA and the internal positive control were degraded (higher $C_T$ value) when the nucleases were active in the freeze-thawed sample or in 10 mM phosphate buffer. The internal positive control could, therefore, be used to determine the efficacy of DNA recovery following sample preparation.

EXAMPLE 24

Validation of Real-Time PCR Estimation of Porphyromonas gingivalis in Periodontal Plaque Sample by Sequence Based Identification Using Real-Time PCR, contribution of Porphyromonas gingivalis in comparison to the total bacterial load in a diseased site periodontal plaque sample was estimated with P. gingivalis specific and universal primers-probe set.

The inventors used a single Universal primer pair to amplify 466 bp fragment of DNA from the DNA isolated from diseased site human periodontal plaque sample. The primers and probes used are in Table 1. Of the 57 clones analyzed, Porphyromonas gingivalis, Bacteroides forsythus, Prevotella tannerae, Rothia dentocariosa were identified to species level, where as Prevotella, Fusobacteria, Catonella, Clostridia, Desulfobubus, Cainpylobacter, Capnocytophaga and Treponema could be identified to genus level. Predominance of P. gingivalis (29.8%) along with Fusobacteria (31.6%) followed by B. forsythlus (10.5%), Prevotella (7%) and Treponema (3.5%) is evident in Sequence based identification (Table 14A). All the other species were represented as one clone per 57 clones analyzed. DNA isolated from same plaque sample was analyzed using Real-Time PCR technology to estimate P. gingivalis number (using P. gingivalis primers-probe set, SEQ ID NOS:7, 8 and 9) in comparison to the total load (using Universal primers-probe set). P. gingivalis cells ($1.4 \times 10^{11}$) against total load ($4.8 \times 10^{11}$) in this diseased site plaque sample showed that P. gingivalis represented 29% of the total load (Table 14B). This example shows the value of the universal primers to trap microbial 16S rDNA for subsequent analysis by sequencing. These data very closely match with the Sequence based identification and validated the two results. Therefore, use of Real-Time PCR technology to estimate the load of P. gingivalis in periodontal plaque sample greatly assists in clinical treatment modality.

EXAMPLE 25

Inhibition of Nuclease Activity and Removal of PCR Inhibitors Improves Efficiency of Quantifying Bacteria by Real-Time PCR Methods for extracting and stabilizing DNA from representatives of a mixed oral flora and comprising the microaerophilic Gram positive organisms, Streptococcus mutans, Lactobacillus acidophilus and Actinomyces israelii, the Gram positive anaerobe Peptostreptococcus micros, and the Gram negative anaerobes, Fusobacterium nucleatum, Porphyromonas endodontalis, Porphyromonas gingivalis and Prevotella melaminogenica, were evaluated for quantitation using Real-Time PCR.

While DNA was easily extracted from the Gram negative organisms and the anaerobic P. micros, microaerophilic Gram positive species required digestion at 56° C. with a combination of lysozyme, mutanolysin and proteinase K. It was noted that P. gingivalis released potent broad spectrum DNAase activity that produced extensive degradation of DNA from all of the test species as well as from an internal positive control derived from the fruit fly B. tyroni. Inhibitors of DNAses were differentially effective and variably inhibitory to the hydrolases necessary for DNA release from Gram positive organisms. A consensus method for this disparate group of organisms was to pre-treat with the nuclease inhibitor diethyl pyrocarbonate (DEPC), digest with hydrolases and add sodium dodecyl sulfate (SDS) to release DNA from the Gram negative and Gram positive organisms. Subsequent purification of the DNA to remove the added DEPC and SDS and other potential PCR inhibitors was also necessary to accurately quantify the DNA, and hence the number of bacteria in a sample. The efficiency of DNA recovery following sample preparation was assessed by including a known amount of exogenous DNA (from *B. tyroni*) in the sample to act as an internal positive control. This standard also provides a control for other combinations of microorganisms where unrecognised nuclease activities may be resistant to DEPC.

The following methods and materials were employed.

(i) Construction of an Internal Positive Control for Real-Time PCR

A chimeric plasmid was constructed to act as an internal positive control. The portion of DNA in the chimeric plasmid that was detected by Real-Time PCR originated from the Queensland fruit fly, *Bactrocerra tryoni* which was obtained from frozen (−80° C.) stocks at the Fruit Fly Research Center, University of Sydney, NSW, Australia. Genomic DNA was extracted from 30 flies (17) and the region between nucleotides 37 and 126 of the dsX gene (GenBank Accession No. AF040077) amplified by PCR (FTS-320 Thermal Sequencer, Corbett Research, NSW, Australia) using 4 μg *B. tryoni* DNA, 100 nM of each of the forward and reverse primers designed for Real-Time PCR detection of this segment of DNA (Table 1), 200 μM of each deoxyribonucleotide triphosphates, 3.5 mM $MgCl_2$ and 2.5 U AmpliTaq Gold in 1×PCR buffer (Applied Biosystems). The PCR reaction was carried out in a volume of 50 μl at 95° C. for 10 min followed by 40 cycles at 95° C. for 15 s and 60° C. for 1 min. The PCR amplicon (89 bp) from the entire 50 μl reaction volume was purified using the Wizard (registered trade mark) PCR Preps DNA Purification System (Promega Corporation, Madison, Wis.). The purified PCR product was cloned into pGEM (registered trade mark)-T Easy Vector (Promega Corporation) according to the manufacturer's instructions. Competent *E. coli* XL blue1 was transformed by electroporation (2.45 V) with the chimeric plasmid using a Bio-Rad Gene Pulser. Recombinants were selected on LB agar plates containing 100 μg ampicillin per ml, 1 mM isopropy-β-D-lthiogalactoside and 100 μg 5-bromo-4-cholro-3-indolyl-β-D-galactoside (X-Gal) per ml. The chimeric plasmids carrying the 89 bp PCR amplicon for the dsX gene were isolated using the Wizard (registered trade mark) Plus SV Minipreps DNA Purification System (Promega Corporation) and termed IPC-BT.

(ii) Design of Primers-probe Sets

For the species specific quantification of *Porphyromonas gingivalis*, a primers-probe set was designed from the 16S rDNA database accessed through the Australian National Genomic Information Service (ANGIS, http://www.angis.org.au). The *P. gingivalis* species specific primers-probe set (SEQ ID NOS:7 and 8) (Table 1) generated a 150 bp amplicon spanning nucleotides 589 to 739 in the *P. gingivalis* 16S rDNA sequence (GenBank Accession No. L16492) with an internal site for the dual labelled fluorogenic probe (SEQ ID NO:9). The primers-probe set fulfilled the recommended guidelines set by Applied Biosystems (Foster City, Calif.).

The design of a universal primers-probe set forth above. The universal primers-probe set (Table 1) generated a 466 bp amplicon spanning residues 331 to 797 on the *E. coli* 16S rRNA gene (GenBank Accession No. ECAT1177T) with an internal site for the dual-labelled fluorogenic probe.

A primers-probe set was also designed to enable the detection of the exogenously added internal positive control, IPC-BT. The primers-probe set (Table 1) was designed from the sequence of dsX gene of *B. tryoni* using Primer Express software (Applied Biosystems). The primers-probe set amplified a 89 bp region spanning nucleotides 37 to 126 on the dsX gene. The probe sequence for the IPC-BT was labelled with the reporter fluorescent dye VIC at the 5' end to differentiate it from the species specific and universal probes which were labelled at the 5' end with the reporter fluorescent dye FAM (Table 1).

(iii) DNA Isolation Procedures

Different methods for releasing DNA by lysing bacteria were assessed. These included:

(a) Sonication:

*P. gingivalis* or *S. mutans* (~$10^9$ cells) were harvested by centrifugation (14,000 g, 2 min, 18-20° C.) and resuspended in 200 μl of 10 mM phosphate buffer pH 6.7 containing 50 mg of glass beads (0.10-0.11 mm diameter) prior to sonication for 5, 10 or 15 min at 75 W using a Branson Sonifier (model 250; Branson Ultrasonics Corporation, Danbury, Conn.). Aliquots (50 μl) collected at each time interval and diluted 1000-fold were used for Real-Time PCR. Quantification of DNA made use of the universal primers-probe set (Table 1) and was based on a standard graph generated by known amounts of *E. coli* DNA as previously described.

(b) Freeze-thaw Method:

*P. gingivalis* or *S. mutans* (~$10^9$ cells) were harvested by centrifugation (14,000 g, 2 min, 18-20° C.), and resuspended in 200 μl of 10 mM phosphate buffer pH 6.7 and frozen at −20° C. After thawing, the sample was diluted 100 fold and a 5 μl aliquot used for Real-Time PCR. Quantification of DNA made use of the universal primers-probe set as described in (a) above.

(c). Freeze-boil Method:

*P. gingivalis* or *S. mutans* cells (~$10^9$ cells) were harvested, resuspended and frozen at −20° C. (2-16 h) as described above before being boiled for 10 min. After cooling to room temperature (18-20° C.), samples were diluted 100-fold and 5 μl aliquots used for Real-Time PCR using the universal primers probe set as described in (a).

(d) Enzymatic Method:

*P. gingivalis* alone or mixed with either *S. mutans* or *E. coli* (~$2.5 \times 10^8$ of each bacterial species) were harvested by centrifugation (14,000 g, 2 min, 18-20° C.) and resuspended in either 45 μl (for *P. gingivalis* cells alone) or 90 μl (for *P. gingivalis* in combination with *S. mutans* or *E. coli* cells) of 10 mM phosphate buffer pH 6.7 containing 1 mg lysozyme $ml^{-1}$ and 1 mg mutanolysin $ml^{-1}$. After incubation at 60° C. for 30 min, the bacteria were lysed in the presence of 1% w/v SDS, before being diluted 100-fold and 5 μl aliquots being used for Real-Time PCR. Quantification of DNA made use of the universal primers-probe set as described in (a).

(e) $ZuCl_2$ Method

*P. gingivalis* alone or mixed with either *S. mutans* or *E. coli* (~$2.5 \times 10^8$ of each bacterial species) were harvested and resuspended as described in (d) above in the presence of 5 mM $ZnCl_2$. After incubation at 60° C. for 30 min the cells were lysed in the presence of 1% w/v SDS, before being diluted 100-fold and 5 μl aliquots being used for Real-Time PCR. Quantification of DNA made use of the universal primers-probe set as described in (a).

(f) Isolation of DNA using ATL Buffer From QIAamp DNA Mini Kit:

Bacterial cultures (~$5 \times 10^8$ of each bacterial species) were pelleted at 13000×rpm at 5 min in Bifuge pico (Heraeus). Cell pellets were resuspended in 180 µl ATL buffer (Qiagen) and 400 µg proteinaseK (Qiagen). The cell suspensions were incubated at 56° C. for 40 min with intermittent vortexing for 10 s after every 10 min. RNase (200 gg) was added, followed by further incubation at 37° C. for 10 min. DNA was purified using QIAamp DNA Mini Kit (Qiagen) as per the manufacturer's instructions.

(g) Isolation of DNA by One Step DEPC Method:

Bacterial cultures (~$5 \times 10^8$ of each bacterial species) were pelleted at 13000×rpm at 5 min in a Bifuge pico (Heraeus). The cell pellet was resuspended in 200 µl buffer containing 10 mM sodium phosphate pH 6.7, 20 mM DEPC, lysozyme (5 mg per ml [final conc.]), mutanolysin (1000 U per 0.48 mg per mil [final conc.]) and 400 µg proteinaseK (Qiagen). The cell suspensions were incubated at 56° C. for 40 min with intermittent vortexing for 10 s after every 10 min. Cells were lysed with SDS (1% w/v [final conc.]). RNase (200 µg) was added, followed by further incubation at 37° C. for 10 min. DNA was purified using a QIAmp DNA Mini Kit (Qiagen) as per the manufacturer's instructions.

(h) Isolation of DNA in Mixed Bacterial Cultures by One Step DEPC Method:

Bacterial cultures (~$2.5 \times 10^8$ of each bacterial species) were pelleted at 13000×rpm at 5 min in a Bifuge pico (Heraeus). Cell pellets were resuspended in 200 µl buffer containing 10 mM sodium phosphate pH 6.7, 20 mM DEPC, lysozyme (5 mg protein per ml [final conc.]), mutanolysin (1000 U per 0.48 mg protein per ml [final conc.]), 400 µg proteinaseK (Qiagen). The cell suspensions were incubated at 56° C. for 40 min with intermittent vortexing for 10 s after every 10 min. Cells were lysed with SDS (1% w/v [final conc.]). RNase (200 µg) was added, followed by further incubation at 37° C. for 10 min. DNA was purified using a QIAmp DNA Mini Kit (Qiagen) as per the manufacturer's instructions.

(i) Isolation of DNA by Two Step DEPC Method:

Bacterial cultures (~$5 \times 10^8$ of each bacterial species) were pelleted at 13000×rpm at 5 min in a Bifuge pico (Heraeus). Cell pellets were resuspended in 144 µl buffer (10 mM sodium phosphate pH 6.7) containing 27.8 mM DEPC. Cell suspensions were incubated on ice for 10 min or sonicated in pulse or continuous mode for 6 min at 75 W using a Branson Sonifier (model 250; Branson Ultrasonics Corporation, Danbury, Conn.) followed by addition of 56 µl of enzyme mix.: [lysozyme (5 mg protein per ml [final conc.]), mutanolysin (1000 U per 0.48 mg protein per ml [final conc.]), containing and 400 µg proteinaseK (Qiagen)]. The cell suspensions were incubated at 56° C. for 40 min with intermittent vortexing for 10 s after every 10 min. Cells were lysed with SDS (1% w/v [final cone.]). RNase (200 µg) was added, followed by further incubation at 37° C. for 10 min. DNA was purified using a QIAmp DNA Mini Kit (Qiagen) as per the manufacturer's instructions.

(iv) Detection of Nuclease Activity

Exogenous, *P. gingivalis* DNA (300-400 ng), purified using QIAmp DNA Mini Kits (see (f) above), was added to samples containing 300-400 ng DNA prepared by lysing bacteria according each of the procedures described in (a)-(c) above prior to incubation at 50° C. for 30 min. Exogenous DNA from *Fusobacterium nucleatum, Porphyromonas endodontalis, Porphyromonas gingivalis, Prevotella melaninogenica* and *Peptostreptococcus micros* and *Escherichia coli* (prepared using ATL buffer and QIAmp DNA Mini Kit) and *Streptococcus mutans* (prepared using one-step DEPC method) were incubated at 50° C. for 30 min with *P. gingivalis* freeze-thaw extract (procedure described in (b)). The degree of DNA degradation was determined visually following electrophoresis of samples on 1% w/v agarose gels.

(v) ZnCl$_2$ as a PCR Inhibitor

In order to determine whether ZnCl$_2$ acted as an inhibitor of Real-Time PCR, DNA was extracted from two sets of duplicate samples of *P. gingivalis* (~$5 \times 10^8$ and ~$5 \times 10^7$ cells) using the protocol described in (e) above. One of each set of duplicate samples of DNA was purified using a QIAmp DNA Mini Kits (QIAGEN). All samples were subsequently diluted to theoretically contain the same amount of DNA before subjecting to analysis by Real-Time PCR using the universal primers-probe set.

(vi) Isolation of *P. Gingivalis* DNA in the Presence of the Internal Positive Control DNA was extracted from *P. gingivalis* ($2.5 \times 10^8$ cells) in the presence of 1 µl IPC-BT, using the protocol described in (e) above. Following appropriate dilution, the amount of *P. gingivalis* DNA and IPC-BT DNA were determined using the specific *P. gingivalis* and IPC-BT primers-probe set, respectively.

(vii) Conditions for Real-Time PCR

Amplification and detection of DNA by Real-Time PCR made use of the ABI PRISM 7700 Sequence Detection System (Applied Biosystems, Foster City, Calif.) using a 96 well plate format. The PCR was carried out in duplicate, in a 25 µl reaction volume containing 300 nM of each of the Universal primers and 100 nM of the Universal probe or 100 nM of each of the primers and probe for the Internal Positive Control (Table 1) using the TaqMan (registered trade mark) PCR Core Reagents Kit (Applied Biosystems). The reaction conditions for amplification of DNA were 95° C. for 10 min, and 40 cycles of 95° C. for 15 s and 60° C. for 1 min. Data was analyzed using the Sequence Detection Software Version 1.6.3 supplied by Applied Biosystems.

(viii) Viable Count

*P. gingivalis* was grown in CDC broth under anaerobic conditions at 37° C. for four days and *S. mutans* was grown 16-18 h in BHI broth at 37° C. under 5% CO$_2$. *P. gingivalis* culture (100 µl), diluted in CDC broth to $10^{-6}$ dilution was plated on CDC agar and incubated under anaerobic conditions at 37° C. for four days and colonies were counted. *S. mutans* culture (100 µl), diluted in BHI broth to $10^{-6}$ dilution was plated on BHI agar and incubated under 5% CO$_2$ at 37° C. for 16-18 h and colonies were counted.

The following results were obtained.

(I) Preparation of Bacterial Cells for the Isolation of DNA

To access all bacterial DNA, the bacterial cell suspensions were sonicated to release DNA for quantification using Real-Time PCR. DNA was released more effectively when the cells were sonicated using glass beads. Effect of sonication was compared with DNA isolation using freeze-thaw and freeze-boil methods. Freeze-thaw method released the least DNA from *P. gingivalis* cells as well as *S. mutans* cells, whereas freeze-boil method released most DNA from *P. gingivalis* cells rather than *S. mutans* cells. This indicated that boiling the samples could be effective method for release of DNA from Gram negative bacteria but not Gram positive bacteria. On the contrary, increase in the sonication time from 5 to 15 minutes, had detrimental effect on the quantification of *P. gingivalis* DNA with no significant change in the quantification of *S. mutans* DNA.

(II) Presence of Nucleases in *P. Gingivalis*

Figure 5B:
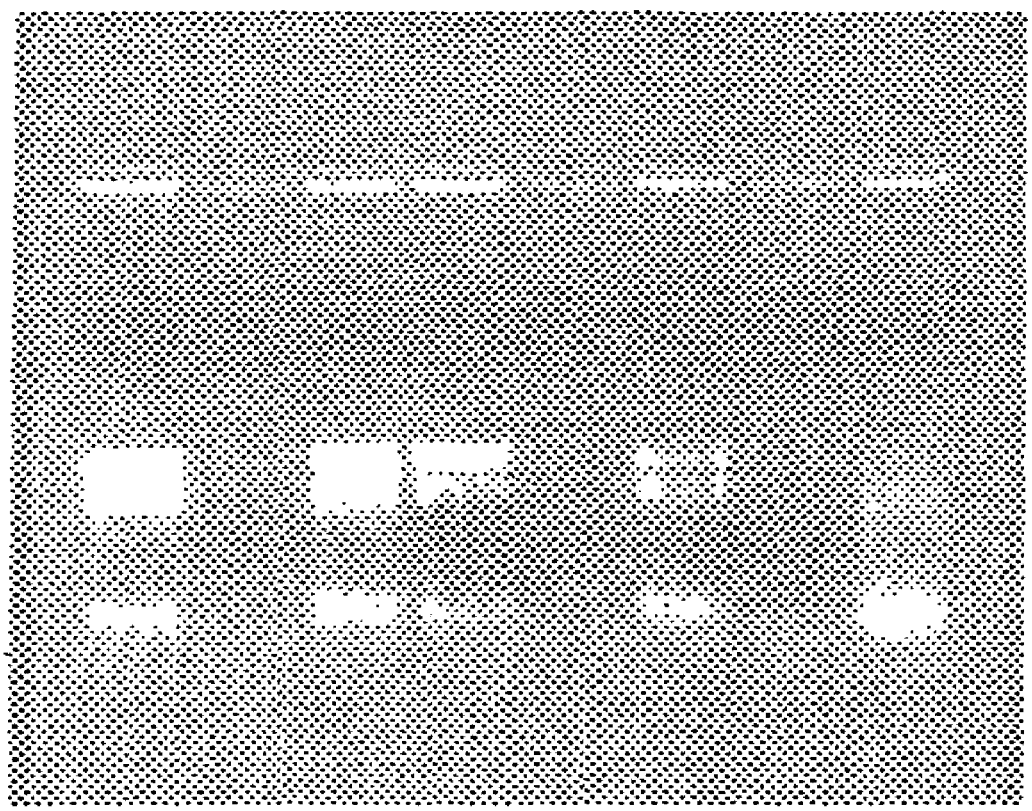
FIG. 5B is a photographic representation showing degradation of DNA by freeze/thawed sample of *P. gingivalis*. (1) *Fusobacterium nucleatum* DNA; (2) *Lactobacillus acidophilus* DNA; (3) *Porphyromonas gingivalis* DNA; (4) *Prevotella melaninogenica* DNA; (5) *Streptococcus mutans* DNA; (6) *Peptostreptococcus micros* DNA; (7) *Porphyromonas endodontalis* DNA; and (8) *Escherichia coli* DNA.

Agarose gel electrophoresis (1% w/v) confirmed the presence of nucleases in *P. gingivalis*. Exogenous *P. gingivalis* DNA was completely degraded and could not be seen when incubated at 50° C. for 30 min in the presence of freeze-thawed *P. gingivalis* culture. However, under the same conditions intact DNA was detected after boiling the frozen *P. gingivalis* culture. Degradation of exogenous *P. gingivalis* DNA in the presence freeze-thawed *P. gingivalis* culture could be prevented by addition of 5 mM $ZnCl_2$ before incubating the samples at 50° C. for 30 min. Exogenous DNA from *Fusobacterium nucleatum, Porphyromonas endodontalis, Porphyromonas gingivalis, Prevotella melaninogenica* and *Peptostreptococcus micros* and *Streptococcus mutans* was completely degraded in the presence of freeze-thawed *P. gingivalis* culture (FIG. 5B).

(III) Protection Against Nuclease Degradation by 5 mM $ZnCl_2$ using the ABI—PRISM Sequence Detection System (ABI-SDS).

DNA isolated from *P. gingivalis* cells in the presence of *E. coli* cells or *S. mutans* cells was quantified on the ABI-SDS using the universal primers-probe set. Significant increase in the amount of DNA quantified was evident for the individual and mixed bacterial populations when the samples were prepared in the presence of 5 mM $ZnCl_2$.

(IV) Effect of $ZnCl_2$ as a PCR Inhibitor

When DNA was isolated in the presence of 5 mM $ZnCl_2$ and diluted 100 fold before using 5 μl on ABI-SDS, $ZnCl_2$ did not inhibit the PCR reaction. As seen in the results for the neat culture, a final concentration of $ZnCl_2$ in the PCR reaction to 0.005 mM caused minimal interference with the amplification reaction and there was no significant change in the amount of DNA quantified before and after the use of the QIAmp DNA Mini Kit. However, dilution of DNA 10 fold (as in the case of 10 fold diluted culture) before using 5 μl on ABI-SDS, resulting in a final concentration of 0.05 mM $ZnCl_2$ in the PCR reaction, prevented the amplification of *P. gingivalis* DNA.

(V) The Internal Positive Control (IPC-BT)

The addition of a chimeric plasmid containing unique non-bacterial DNA to mixed bacteria samples allowed both the determination of the efficiency of DNA recovery following sample preparation and the detection of potential PCR inhibitors in the reaction mix during Real-Time PCR. *B. tryoni* dsX gene insert in pGEM (registered trade mark)-T Easy was confirmed by PCR which generated an 89 bp amplicon visualized on 2% w/v agarose gel electrophoresis.

(VI) Isolation of *P. gingivalis* DNA in the Presence of IPC-BT

Due to limitation of the software, the standard graph generated by FAM labeled probes (*P. gingivalis* or universal) could not be used to quantify IPC-BT, as the reporter dye on the probe for detection of IPC-BT is VIC labeled. This necessitated the results to be expressed in terms of $C_T$ values. Isolation of *P. gingivalis* DNA in the presence of the Internal Positive Control and the effect of nucleases on the quantification (expressed as $C_T$ values) is shown in Table 8. *P. gingivalis* DNA and IPC-BT were degraded at the same time by the action of the bacterial nucleases present in the sample when DNA was isolated by freeze-thaw method or in the absence of $ZnCl_2$ (higher $C_T$ value). On the contrary, isolation of DNA by the freeze-boil method or $ZnCl_2$ method protected against degradation of DNA by the nucleases (lower $C_T$ value). Multiplexing the same samples showed no significant variation on the levels of *P. gingivalis* DNA and IPC-BT in terms of $C_T$ values (Table 8).

(VII) Isolation of DNA using ATL Buffer Front QIAamp DNA Mini Kit

ATL buffer from the QIAamp DNA Mini kit could recover DNA from the Gram negative bacteria *Fusobacterium nucleatum, Porphyromonas endodontalis, Porphyromonas gingivalis, Prevotella melaminogenica* and the anaerobic Gram positive bacterium, *Peptostreptococcus micros*. However, DNA recovery from *Streptococcus mutans, Actinomyces israeli* and *Lactobacillus acidophilus* was almost negligible (Table 9).

(VIII) Isolation of DNA by One Step DEPC Method

As can be seen (Table 10), in the absence of DEPC, *Porphyromonas gingivalis* DNA is significantly degraded. Recovery of DNA from *Streptococcus mutans* improved more than 10-fold due to the cell wall treatment. However, the amount of DNA recovered from *Peptostreptococcus micros* dropped by about 5-fold in the presence of DEPC. DNA recovery from the remaining bacteria in this group remained comparatively unaffected.

(IX) Comparison of Viable Count of *P. gingivalis* and *S. mutans* Cells Based on Isolation of DNA by One Step DEPC Method Efficiency of DNA recovery by the ATL method and one-step DEPC method and the number of *P. gingivalis* cells calculated based on these values were comparable. However, the viable count was 10-fold less than the relative number of cells estimated based on Real-Time PCR. For *S. mutans* the number of viable cells per ml were comparable with the number of cells per ml estimated, based on Real-Time PCR (Table 11).

(X) Isolation of DNA in Mixed Bacterial Cultures by One Step DEPC Method

In the absence of DEPC, the mixed culture reported lower recovery of DNA as compared to the presence of DEPC during DNA isolation (Table 12). (XI) Isolation of DNA by Two Step DEPC Method Incubation of bacterial suspensions in the presence of DEPC prior to cell wall treatment enzymes improved the recovery of DNA from *Peptostreptococcus micros* (compare data in Table 10 with that in Table 13). Sonication for a 6 min. pulse (rather than continuous sonication) improved the recovery of *A. israelii* DNA by 3-fold and the amount of DNA recovered from all the other bacteria was comparable (compare data in Table 10 with that in Table 13).

EXAMPLE 26

Sequence Based Identification of Bacteria from Dental Plaque Flora

The present method involves culturing bacteria from dental plaques and determining that they could not be readily identified by standard culture techniques. DNA is isolated by the two-step DEPC method and subjected to PCR using the universal primers. The amplified product is purified and sequenced and subjected to BLAST/GAP analysis.

Figure 9A:
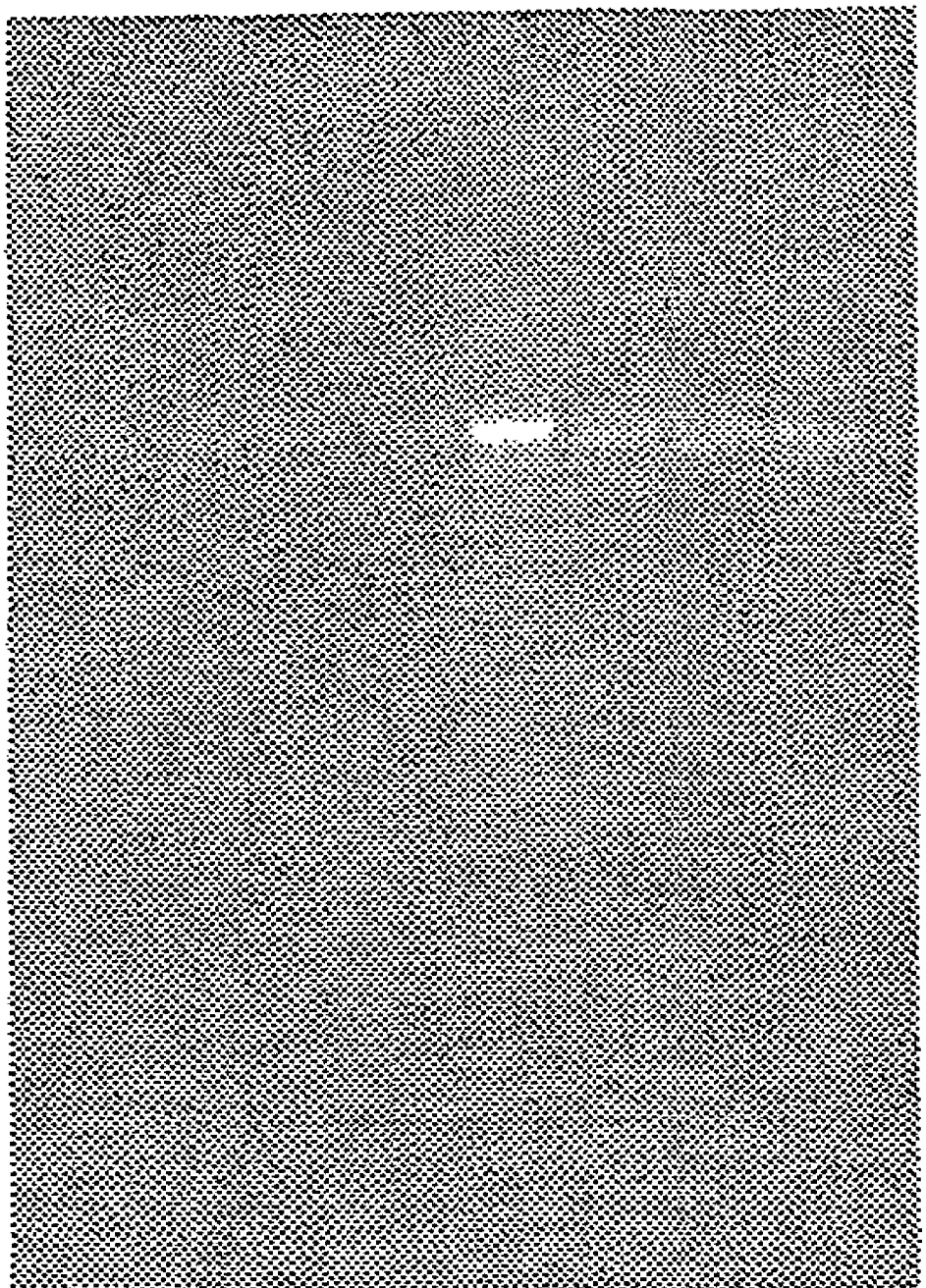
FIG. 9A is a photographic representation showing isolation of DNA using ATL buffer and two-step DEPC method: bacteria identified as Streptococci. (1) *S. mitis* using ATL buffer; (2) *S. intermedius* using ATL buffer; (3) *S. intermedius* using ATL buffer; (4) *S. costellatus* using ATL buffer; (5) *S. mitis* using two-step DEPC method; (6) *S. intermedius* using two-step DEPC method; (7) *S. intermedius* using two-step DEPC method; and (8) *S. costellatus* using two-step DEPC method.
Figure 9B:
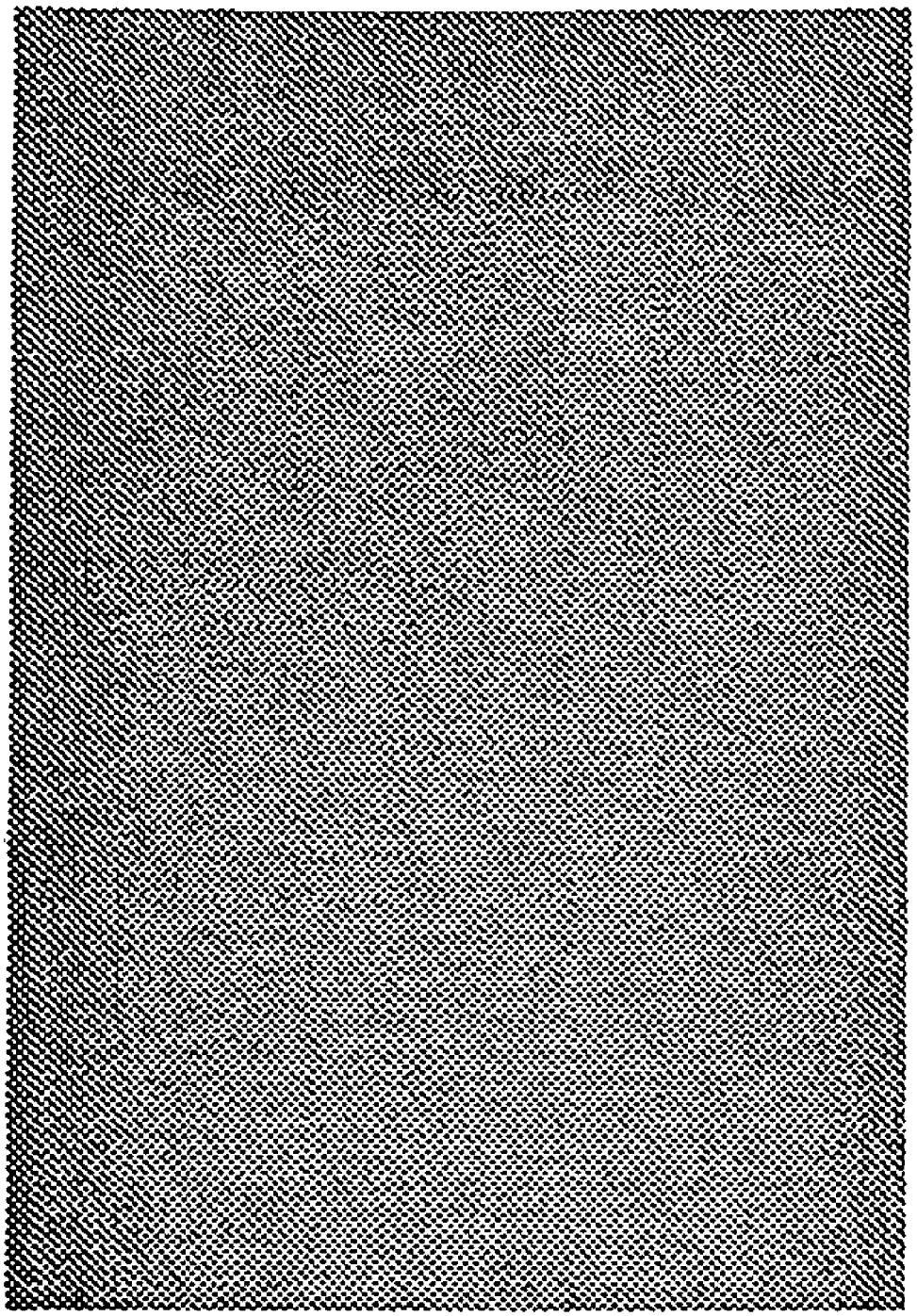
FIG. 9B is a photographic representation showing isolation of DNA using ATL buffer and two-step DEPC method: bacteria identified as Actinomyces. (1) *A. viscosus* by ATL method; (2) *A. viscosus* by two-step DEPC method; (3) *A. georgiae* by ATL method; and (4) *A. georgiae* by two-step DEPC method.

Specifically, DNA was isolated from bacterial cultures using two-step DEPC method. PCR reaction was run using universal primer set. Amplified product 466 bp was purified and sequenced using universal forward primer. DNA sequence (431 bp for 4-2, 400 bp for 2-2-1 and 1-2-1, 386 bp for 6-5 and 10-34 and 382 bp for 4-2-1) was BLAST searched using NR nucleic database through WebANGIS. High score bacterial sequences were subjected to GAP program to ascertain % similarity and % identity. Identification of the culture was based on more than 98.5-99% identical sequences (as specified with identification number) using the amplicon length for each culture as stated. The results are shown in Table 15. Furthermore, the isolation of Streptococcus and Actinomyces DNA is shown in FIGS. 9A and 9B.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

Representative bacterial species[a] detected by Real-Time PCR using the universal primer-probe set and estimated bacterial numbers based on standard graph for *E. coli* DNA

| Bacterial species | $c_t$ | DNA (pg)/ 25 µl | No. of bacteria[b]/ 25 µl | No. of bacteria/ pg DNA[c] |
|---|---|---|---|---|
| Gram negative aerobic bacteria | | | | |
| *Pseudomonas aeruginosa* ATCC 19660 | 18.14 | 1240 | $250 \times 10^3$ | $2.02 \times 10^2$ |
| *Legionella pneumophilia* knoxville-1 ATCC 33153 | 21.93 | 161.5 | $33 \times 10^3$ | $2.04 \times 10^2$ |
| Gram negative facultative anaerobic bacteria | | | | |
| *Escherichia coli* JM109 | 19.86 | 444 | $89 \times 10^3$ | $2.00 \times 10^2$ |
| *Serratia marsescens* ATCC 274 | 20.96 | 224 | $45 \times 10^3$ | |
| Gram negative anaerobic bacteria | | | | |
| *Porphyromonas gingivalis* ATCC 33277 | 23.5 | 65 | $13 \times 10^3$ | $2.00 \times 10^2$ |
| *Prevotella melaninogenica* ATCC 25845 | 20.48 | 364 | $73 \times 10^3$ | $2.00 \times 10^2$ |
| *Fusobacterium nucleatum* ATCC 25586 | 21.05 | 262 | $53 \times 10^3$ | $2.02 \times 10^2$ |

TABLE 1

Primers and probes

| Primers or Probe | Sequence (5'-3') | | $T_m$ (° C.) |
|---|---|---|---|
| Universal forward primer | TCCTACGGGAGGCAGCAGT | [SEQ ID NO:1] | 59.4 |
| Universal reverse primer | GGACTACCAGGGTATCTAATCCTGTT | [SEQ ID NO:2] | 58.1 |
| Universal probe | [6-FAM]CGTATTACCGCGGCTGCTGGCAC[TAMRA] | [SEQ ID NO:3] | 69.9 |
| B. tryoni forward primer | GGAAGGTAAGTTGCATTTCAGCA | [SEQ ID 110:4] | 59.3 |
| B. tryoni reverse primer | GCGTACTTATCATGGTAAATTAAGTCAATT | [SEQ ID NO :5] | 58.6 |
| B. tryoni probe | [VIC]-TCCCGTTACAAAATCGTGTTTACATCGTATACTCG-[TAMRA] | [SEQ ID NO:6] | 69.1 |
| P. gingivalis forward primer | TCGGTAAGTCAGCGGTGAAAC | [SEQ ID NO: 7] | 58.8 |
| P. gingivalis reverse primer | GCAAGCTGCCTTCGCAAT | [SEQ ID NO: 8] | 58.7 |
| P. gingivalis probe | [6-FAM]CTCAACGTTCAGCCTGCCGTTGAAA[TAMRA] | [SEQ ID NO:9] | 68.8 |

6-FAM: 6-carboxyfluorescene;
TAMRA: 6-carboxy-tetramethyirhodamine
VIC: Proprietory dye of Applied Biosystems

TABLE 2-continued

Representative bacterial species[a] detected by Real-Time PCR using the universal primer-probe set and estimated bacterial numbers based on standard graph for E. coli DNA

| Bacterial species | $c_t$ | DNA (pg)/ 25 μl | No. of bacteria[b]/ 25 μl | No. of bacteria/ pg DNA[c] |
|---|---|---|---|---|
| Gram positive bacteria | | | | |
| *Staphylococcus aureus* ATCC 12600 | 16.15 | 3975 | $801 \times 10^3$ | $2.02 \times 10^2$ |
| *Streptococcus mutans* LT11 | 18.78 | 950 | $192 \times 10^3$ | $2.02 \times 10^2$ |
| *Peptostreptococcus micros* ATCC 33270 | 22.83 | 96 | $19 \times 10^3$ | $1.98 \times 10^2$ |
| Gram positive asporogenous bacteria | | | | |
| *Lactobacillus acidophilus* ATCC 4356 | 20.73 | 312 | $63 \times 10^3$ | $2.02 \times 10^2$ |
| Actinomyces | | | | |
| *Actinomyces israelii* ATCC 12102 | 26.38 | 13 | $2.6 \times 10^3$ | $2.00 \times 10^2$ |
| *Mycobacterium tuberculosis* H37RV | 26 | 11 | $2.2 \times 10^3$ | $2.00 \times 10^2$ |

[a]Order of microbes is based on Bergy's Manual of Determinative Bacteriology (12).
[b]Estimated from the theoretical value: 0.496 picogram E. coli DNA = 100 E. coli cells.
[c]No. of bacteria/pg DNA remains constant for almost all the bacteria since all values are interpolated from the standard graph using E. coli DNA. However, based on the size of the genome, no. of bacteria/pg DNA would differ. Each DNA sample was diluted accordingly to be within the $C_T$ range of the standard graph and the mean quantity was estimated by the machine from the duplicates.

TABLE 3

Specificity of the universal primer-probe set for individual bacterial strains[a] tested for Real-Time PCR and estimation of bacterial numbers based on standard graph for E. coli DNA

| Bacterial species | $c_t$ | DNA (pg)/ 25 μl | No. of bacteria[b]/ 25 μl | No. of bacteria/ pg DNA[c] |
|---|---|---|---|---|
| Gram negative aerobic bacteria | | | | |
| *Pseudomonas aeruginosa* ATCC 15442 | 18.46 | 1015 | $205 \times 10^3$ | $2.02 \times 10^2$ |
| *Pseudomonas aeruginosa* 6294 | 18.26 | 1130 | $228 \times 10^3$ | $2.02 \times 10^2$ |
| *Pseudomonas aeruginosa* 6206 | 19.67 | 485 | $98 \times 10^3$ | $2.02 \times 10^2$ |
| *Pseudomonas fluorescens* | 19.19 | 650 | $131 \times 10^3$ | $2.02 \times 10^2$ |
| *Pseudomonas putida* | 22.35 | 98 | $20 \times 10^3$ | $2.04 \times 10^2$ |
| *Pseudomonas stutzeri* | 18.87 | 790 | $159 \times 10^3$ | $2.01 \times 10^2$ |
| *Pseudomonas alcaligens* | 19.33 | 615 | $124 \times 10^3$ | $2.02 \times 10^2$ |
| Pseudomonas species | 19.52 | 530 | $107 \times 10^3$ | $2.02 \times 10^2$ |
| *Legionella pneumophila* serogroup 4 ATCC 33156 | 21.34 | 223 | $45 \times 10^3$ | $2.02 \times 10^2$ |
| *Legionella pneumophila* serogroup 5 ATCC 33216 | 20.08 | 477 | $96 \times 10^3$ | $2.01 \times 10^2$ |
| *Legionella pneumophila* serogroup 6 ATCC 33215 | 21.19 | 228 | $46 \times 10^3$ | $2.02 \times 10^2$ |
| *Legionella pneumophila* philadelphia-1 ATCC 33152 | 25.18 | 25 | $5.1 \times 10^3$ | $2.04 \times 10^2$ |
| *Legionella anisa* | 24.02 | 49 | $9.9 \times 10^3$ | $2.02 \times 10^2$ |
| *Legionella bozemanii* serogroup 2 | 21.46 | 209 | $42 \times 10^3$ | $2.01 \times 10^2$ |
| *Legionella londiniensis* | 20.5 | 361 | $73 \times 10^3$ | $2.02 \times 10^2$ |
| *Legionella macearchernii* | 22.97 | 90 | $18 \times 10^3$ | $2.00 \times 10^2$ |
| *Legionella waltersii* | 21.96 | 158 | $32 \times 10^3$ | $2.02 \times 10^2$ |
| Gram negative facultative anaerobic bacteria | | | | |
| *Escherichia coli* NM5222 | 28.22 | 2.9 | $0.59 \times 10^3$ | $2.03 \times 10^2$ |
| *Escherichia coli* XL 1 blue | 26.95 | 6.3 | $1.3 \times 10^3$ | $2.06 \times 10^2$ |
| Gram negative anaerobic bacteria | | | | |
| *Porphyromonas endodontalis* ATCC 35406 | 22.05 | 148 | $30 \times 10^3$ | $2.02 \times 10^2$ |
| *Fusobacterium necrophorum* ATCC 252 | 23.15 | 81 | $16 \times 10^3$ | $1.98 \times 10^2$ |
| Gram positive bacteria | | | | |
| *Staphylococcus aureus* ATCC 9144 | 29.57 | 1.31 | $0.27 \times 10^3$ | $2.06 \times 10^2$ |
| *Staphylococcus aureus* ATCC 12598 | 27.41 | 4.77 | $0.96 \times 10^3$ | $2.01 \times 10^2$ |
| *Staphylococcus aureus* ATCC BM 10458 | 26.32 | 13 | $2.7 \times 10^3$ | $2.07 \times 10^2$ |
| *Staphylococcus aureus* ATCC BM 10143 | 27.20 | 5.35 | $1.1 \times 10^3$ | $2.05 \times 10^2$ |
| *Staphylococcus epidermidis* ATCC 35983 | 17.88 | 1405 | $2.83 \times 10^3$ | $2.01 \times 10^2$ |
| *Staphylococcus epidermidis* ATCC 14990 | 22.27 | 102 | $21 \times 10^3$ | $2.05 \times 10^2$ |
| *Staphylococcus hemolyticus* ATCC 29970 | 21.14 | 201 | $41 \times 10^3$ | $2.04 \times 10^2$ |
| *Staphylococcus hemolyticus* | 22.28 | 112.5 | $23 \times 10^3$ | $2.04 \times 10^2$ |
| *Staphylococcus schleferi* ATCC 43808 | 22.29 | 102 | $21 \times 10^3$ | $2.05 \times 10^2$ |
| *Streptococcus sanguis* H1 | 17.05 | 2495 | $503 \times 10^3$ | $2.01 \times 10^2$ |
| *Streptococcus saltvarlus* | 20.27 | 410 | $83 \times 10^3$ | $2.02 \times 10^2$ |
| *Streptococcus gordonii* | 20.03 | 466 | $94 \times 10^3$ | $2.02 \times 10^2$ |
| *Peptostreptococcus anaerobius* ATCC 27337 | 22.36 | 125 | $25 \times 10^3$ | $2.00 \times 10^2$ |
| Gram positive asporogenous bacteria | | | | |
| *Lactobacillus rhamnosus* ATCC 7469 | 24.53 | 37 | $7.5 \times 10^3$ | $2.02 \times 10^2$ |
| Actinomyces | | | | |
| *Actinomyces neslundii* ATCC 12104 | 24.32 | 42 | $8.4 \times 10^3$ | $2.00 \times 10^2$ |

[a]Order of microbes is based on Bergy's Manual of Determinative Bacteriology (12).
[b]Estimated from the theoretical value: 0.496 picogram E. coli DNA = 100 E. coli cells. Each DNA sample was diluted accordingly within the $c_t$ range of the standard graph.
[c]No. of bacteria/pg DNA remains constant for almost all the bacteria since all values are interpolated from the standard graph using E. coli DNA. However, based on the size of the genome, no. of bacteria/pg DNA would differ. Each DNA sample was diluted accordingly to be within the $C_T$ range of the standard graph and the mean quantity was estimated by the machine from the duplicates.

TABLE 4

Effect of species specific DNA standards on the relative estimation of [DNA] using the universal primers-probe set for Real-Time PCR

| | Relative amount of DNA (%)* | | | | | |
|---|---|---|---|---|---|---|
| Bacterium | $A_{260}$ nm† | S. aureus DNA standard | E. coli DNA standard | P. aeruginosa DNA standard | P. endodontalis DNA standard | P. melaninogenica DNA standard |
| S. aureus | 100 | 106 | 145 | 294 | 1231 | 2600‡ |
| E. coli | 100 | 46 | 96 | 139 | 550 | 1415 |
| P. aeruginosa | 100 | 48 | 96 | 139 | 456 | 688 |
| P. endodontalis | 100 | 8 | 17 | 9 | 108 | 193 |
| P. melaninogenica | 100 | 5 | 11 | 10 | 68 | 110 |

*The species specific standard DNA graphs ($c_t$ vs [DNA]) were generated from E. coli DNA within the range 238 fg–2.38 ng, from P. aeruginosa DNA within the range 25 fg–2.5 ng, from S. aureus DNA within the range 27.5 fg–2.75 ng, from P. melaninogenica DNA within the range 1.12 pg–112 ng and from P. endodontalis DNA within the range 240 fg–24 ng. The mean of duplicate determinations are shown. Variation between duplicates was ≦2.7% except where underlined where the values for the E. coli and P. melaninogenica DNA standard varied by 4.8% and that for the P. aeruginosa DNA standard by 15.9%.
†The concentration of DNA was determined spectrophotometrically and normalized to 100% prior to diluting in the range of 100- to 1000-fold for determination by Real-Time PCR.
‡Value halved from that determined by computer software (for explanation, see text).

TABLE 5

Enumeration of bacterial cell numbers by viable cell count and Real-Time PCR.

| Bacterial Culture | Viable. cell count* [cells (ml culture)$^{-1}$] | Relative estimation of cell numbers by Real-Time PCR† [cells (ml culture)$^{-1}$] |
|---|---|---|
| E. coli | $6.5 \times 10^8$ | $6.7 \times 10^8$ |
| P. aeruginosa | $3.3 \times 10^9$ | $4.2 \times 10^9$ |
| S. aureus | $1.3 \times 10^8$ | $2.5 \times 10^9$ |
| Mixed culture‡ | $1.5 \times 10^{9}$§ | $\underline{1.3 \times 10^9}$ |

*The data are the means of duplicate determinations. Variation between duplicates was ≦5.2%.
†Based on a standard graph generated by E. coli DNA within the range 238 fg-2.38 ng. The mean of duplicate determinations for each of two dilutions of DNA are shown. Variation between duplicates did not exceed 3.0% except for one dilution of the underlined where the variation was 8.8%.
‡The mixed culture consisted of equal volumes of E. coli, P. aeruginosa and S. aureus cultures.
§Estimated from the viable cell numbers measured in each of the three cultures.

TABLE 6

Real-Time PCR estimation of anaerobic bacteria in carious dentine compared with the total viable anaerobic load*

| Sample | Estimation of Gram-negative bacteria by Real-Time PCR† [cells (mg dentine)$^{-1}$] | Viable colony forming units‡ [CFU (mg dentine)$^{-1}$] | Ratio§ [cells/CFU] |
|---|---|---|---|
| 1 | $3.4 \times 10^8$ | $9.0 \times 10^6$ | 38 |
| 2 | $\underline{4.5 \times 10^8}$ | $5.5 \times 10^6$ | 82 |
| 3 | $4.8 \times 10^8$ | $9.8 \times 10^6$ | 49 |
| 4 | $1.3 \times 10^8$ | $4.8 \times 10^6$ | 27 |
| 5 | $3.8 \times 10^8$ | $1.2 \times 10^7$ | 32 |
| 6 | $\underline{5.5 \times 10^8}$ | $1.2 \times 10^7$ | 46 |
| 7 | $1.4 \times 10^8$ | $6.9 \times 10^6$ | 21 |
| 8 | $1.1 \times 10^8$ | $2.0 \times 10^6$ | 55 |
| 9 | $1.9 \times 10^8$ | $1.5 \times 10^7$ | 13 |
| 10 | $3.7 \times 10^8$ | $2.2 \times 10^7$ | 17 |
| 11 | $\underline{1.4 \times 10^8}$ | $3.1 \times 10^6$ | 45 |
| 12 | $3.6 \times 10^8$ | $5.9 \times 10^6$ | 61 |
| 13 | $1.5 \times 10^8$ | $2.2 \times 10^6$ | 68 |
| 14 | $1.1 \times 10^9$ | $1.2 \times 10^7$ | 92 |
| 15 | $\underline{2.6 \times 10^8}$ | $1.4 \times 10^7$ | 19 |
| 16 | $\underline{2.5 \times 10^8}$ | $1.5 \times 10^7$ | 17 |
| 17 | $\underline{2.8 \times 10^8}$ | $8.2 \times 10^6$ | 34 |
| 18 | $\underline{6.5 \times 10^8}$ | $1.6 \times 10^7$ | 41 |
| 19 | $\underline{2.5 \times 10^8}$ | $5.6 \times 10^6$ | 45 |
| 20 | $\underline{6.7 \times 10^8}$ | $3.7 \times 10^7$ | 18 |

*The method of DNA extraction lyses anaerobic Gram-negative and Gram-positive bacteria, but not facultative Gram-positive bacteria.
†Based on a standard graph generated by P. melaninogenica DNA within the range 82.9 fg-8.29 ng where 2.36 fg P. melaninogenica DNA represents one cell. The data are the means of triplicate determinations. The standard deviation of the means varied by <1.0% except for the underlined where the variation was in the range of 1.7-4.4%.
‡The data are the means of duplicate determinations. Variation between duplicates was <10.0%.
§The ratio represents the n-fold increase in anaerobic bacteria detected by Real-Time PCR over the total colony count which includes facultative Gram-positive bacteria.

TABLE 7

| Sample Conditions | $C_T$ value P. gingivalis DNA | $C_T$ value Internal positive control |
|---|---|---|
| Freeze/thaw | 24 | 26.2 |
| Freeze/boil | 16 | 16.6 |
| Enzymatic | 21.5 | 20.4 |
| Enzymatic + 5 mM Zn Cl2 10 mM phosphate + 5 mM Zn Cl2 | 16.5 | 17.2 |

TABLE 8

Isolation of *P. gingivalis* DNA in the presence of Internal Positive Control (IPC-BT)[a]

| DNA isolation method | $C_T$[b] value (FAM)[c] | | $C_T$[b] value (VIC)[d] | |
|---|---|---|---|---|
| | *P. gingivalis* DNA | Multiplex[e] | IPC-BT DNA | Multiplex[e] |
| Freeze-thaw | 23.52 | 22.6 | 27.6 | 27.6 |
| Freeze-boil | 16.3 | 16.6 | 16.3 | 15.9 |
| Enzymatic | 20.9 | 19.8 | 21.6 | 21.9 |
| Enzymatic + $ZnCl_2$ | 16.05 | 15.5 | 16.8 | 16 |

[a]Input value of the Internal Positive Control (IPC-BT) was at $C_T$: 16
[b]Threshold cycle: Higher $C_T$ values indicates low amount of DNA and lower $C_T$ indicates high amount of DNA
[c]Only reporter dye FAM is read
[d]Only reporter dye VIC is read
[e]Same PCR reaction-well contained the primers and probe sets for *P. gingivalis* as well as IPC-BT

TABLE 9

Estimation of DNA following extraction in ATL buffer from QIAmp DNA Mini Kit (Real-Time PCR quantification)

| Bacteria | Amount of DNA (pg) |
|---|---|
| *Fusobacterium nucleatum* | 507 |
| *Porphyromonas endodontalis* | 251 |
| *Porphyromonas gingivalis* | 921 |
| *Prevotella melaninogenica* | 270 |
| *Peptostreptococcus micros* | 83.8 |
| *Streptococcus mutans* | 41.2 |
| *Lactobacillus acidophilus* | 25.0 |
| *Actinomyces israelii* | 0.269 |

TABLE 10

Estimation of DNA following one-step DEPC method (Real-Time PCR quantification)

| | Amount of DNA (pg) | |
|---|---|---|
| Bacteria | Absence of DEPC: | Presence of DEPC: |
| *Fusobacterium nucleatum* | 457 | 295 |
| *Porphyromonas endodontalis* | 255 | 193 |
| *Porphyromonas gingivalis* | 8.59 | 371 |
| *Prevotella melaninogenica* | 114 | 124 |
| *Peptostreptococcus micros* | 63.9 | 18.2 |
| *Streptococcus mutans* | 708 | 550 |
| *Lactobacillus acidophilus* | 115 | 76.7 |
| *Actinomyces israelii* | 1.83 | 1.53 |

TABLE 11

Comparison of viable count of *P. gingivalis* and *S. mutans* cells with relative amount of cells estimated by Real-Time PCR and number of cells calculated based on DNA measurement at A260 as a measure of recovery of DNA

| Culture | Viable count[a] per ml | Relative number of cells[b] per ml based on Real-Time PCR | | Number of cells per ml based on $A_{260}$ | |
|---|---|---|---|---|---|
| | | ATL method | One-step DEPC method | ATL method | One-step DEPC method |
| *P. gingivalis* | $1.75 \times 10^8$ | $4.1 \times 10^9$ | $3.4 \times 10^9$ | $4.8 \times 10^9$ | $5.6 \times 10^9$ |
| *S. mutans* | $5.4 \times 10^9$ | One-step DEPC method $6.0 \times 10^9$ | | One-step DEPC method $9.3 \times 10^9$ | |

[a]*P. gingivalis* culture grown on CDC agar plate under anaerobic conditions and *S. mutans* culture grown on BHI agar plate under 5% $CO_2$.
[b]Using *P. gingivalis* DNA as a standard graph (3600 pg to 0.36 pg range) considering 100 *P. gingivalis* cells = 0.250 pg DNA and 100 *S. mutans* cells = 0.237 pg DNA.

TABLE 12

Estimation of DNA in mixed bacterial culture following extraction by one-step DEPC method (Real-Time PCR quantification)

| | Amount of DNA (pg) reaction using Universal primers-probe | | Amount of DNA (pg) reaction using *P. gingivalis* primers-probe | |
|---|---|---|---|---|
| Bacteria | Absence of DEPC: | Presence of DEPC: | Absence of DEPC: | Presence of DEPC: |
| *Fusobacterium nucleatum* + *Porphyromonas gingivalis* | 107 | 392 | 35.9 | 188 |
| *Prevotella melaninogenica* + *Porphyromonas gingivalis* | 90 | 323 | 44.2 | 232 |
| *Streptococcus mutans* + *Porphyromonas gingivalis* | 474 | 493 | 59.4 | 249 |

TABLE 13

Estimation of DNA following extraction by two-step DEPC method (Real-Time PCR quantification)

| | Amount of DNA (pg) following extraction | | |
|---|---|---|---|
| Bacteria | On ice | Sonicated with pulse | Continuously sonicated |
| *Fusobacterium nucleatum* | 319 | 276 | 123 |
| *Porphyromonas endodontalis* | 198 | 153 | 122 |
| *Porphyromonas gingivalis* | 327 | 312 | 410 |
| *Prevotella melaninogenica* | 58.3 | 82.2 | 67.8 |
| *Peptostreptococcus micros* | 66.7 | 59.4 | 64.7 |
| *Streptococcus mutans* | 471 | 437 | 361 |
| *Lactobacillus acidophilus* | 85.5 | 80.5 | 44.4 |
| *Actinomyces israelii* | 2.47 | 4.74 | 3.01 |

TABLE 14A

Relative estimation of *P. gingivalis* cells and total bacteria in diseased site plaque sample

| Condition | Plaque No. | Relative No. of cells estimated per ml of plaque sample | | % *P. gingivalis* |
|---|---|---|---|---|
| | | *P. gingivalis* | Total load | |
| Diseased site plaque sample | 45 | $1.4 \times 10$ | $4.8 \times 10^{11}$ | 29 |

*P. gingivalis* DNA (3600 pg-0.36 pg) was used for the standard graph for relative estimation of DNA in the plaque samples.
100 *P. gingivalis* cells = 0.250 pg DNA.

TABLE 14B

Diversity of species in 57 clones analyzed for Sequenced Based Identification using 466 bp DN segment amplified using universal primers

| Bacteria | No. of species | % |
|---|---|---|
| *P. gingivalis* | 17 | 29.8 |
| Fusobacteria | 18 | 31.6 |
| *B. forsythus* | 6 | 10.5 |
| Prevotella | 4 | 7 |
| Treponema | 2 | 3.5 |
| Campylobacter | 1 | 1.8 |
| Capnocytophaga | 1 | 1.8 |
| Desufobulbus | 1 | 1.8 |
| Catonella (clostridium) like | 1 | 1.8 |
| Streptococcus | 1 | 1.8 |
| Clostridium | 1 | 1.8 |
| Porphyromonas like | 1 | 1.8 |
| *Rothia dentocariosa* | 1 | 1.8 |
| Flexistipes like | 1 | 1.8 |
| Uncultured bacterium | 1 | 1.8 |

TABLE 15

Sequence based identification of bacteria from dental plaque flora

| Culture | High score bacterial species | % Similarity | % Identity |
|---|---|---|---|
| 4-2 | *S. mitis* SM16SRR1 | 99.3 | 99.3 |
| | *S. costellatus* AF104677 | 94 | 94 |
| | *S. anginosus* AF306833 | 94 | 94 |
| | *S. intermedius* AF104673 | 94.4 | 94.4 |
| 2-2-1 | *S. mitis* SM16SRR1 | 94.5 | 93.7 |
| | *S. costellatus* AF104677 | 98.24 | 97.49 |
| | *S. anginosus* AF306833 | 98.74 | 97.99 |
| | *S. intermedius* AF104673 | 99.50 | 98.74 |
| 6-5 | *S. mitis* SM16SRR1 | 94.8 | 94.5 |
| | *S. costellatus* AF104677 | 98.7 | 98.4 |
| | *S. anginosus* AF306833 | 99.2 | 98.96 |
| | *S. intermedius* AF104673 | 100 | 99.74 |
| 10-34 | *S. mitis* SM16SRR1 | 94.56 | 94.3 |
| | *S. costellatus* AF104677 | 100 | 99.74 |
| | *S. anginosus* AF306833 | 98.45 | 98.19 |
| | *S. intermedius* AF104673 | 98.7 | 98.45 |
| 1-2-1 | Actinomyces species oral clone AF385553 | 99.24 | 98.49 |
| | *A. viscosus* AVRRNA16S | 98.99 | 98.24 |
| | *A. naeslundii* ANE234051 | 98.995 | 97.99 |
| | *A. meyeri* AMRNAR16S | 92.68 | 91.92 |
| | *A. georgiae* AG16SRRNA | 92.93 | 92.17 |
| | *A. odontolyticus* AOD234041 | 91.41 | 90.68 |
| 4-2-1 | Actinomyces species oral clone | 93.42 | 93.16 |
| | *A. viscosus* AVRRNA16S | 93.16 | 92.90 |
| | *A. naeslundii* ANE234051 | 93.95 | 93.42 |
| | *A. meyeri* AMRNAR16S | 98.42 | 98.16 |
| | *A. georgiae* AG16SRRNA | 99.74 | 99.47 |
| | *A. odontolyticus* AOD234041 | 97.63 | 97.37 |

BIBLIOGRAPHY

1. Amann et al, 1995, *Microbiol Rev.* 59: 143-169.
2. Ward et al., 1990, *Nature* 345: 63-65.
3. Hugenholtz et al., 1998, *J. Bacteriol.* 180: 4765-4774.
4. Veal et al., 2000, *J. Immunol. Methods* 243: 191-210.
5. Attfield et al., 1999, *Australas Biotechnol.* 9: 159-166.
6. Wintzingerode et al., 1997, *FEMS Microbiol. Reviews* 21: 213-229
7. Blok et al., 1997, *Biotechniques* 22: 700-704.
8. Rupf et al., 1999, *J. Dent. Res.* 78: 850-856.
9. Heid et al., 1996, *Genome Res.* 6: 986-994.
10. U.S. Department of Health and Human Services-Centres for Disease Control, 1982, Media for the isolation, characterization and identification of obligately anaerobic bacteria. Washington D.C., USGPO.
11. Johnson et al., 1995, *J. Clin. Microbiol.* 33: 755-758.
12. Holt et al., 1994, Bergey's Manual (registered trade mark) of Determinative Bacteriology, Ninth ed., The Williams & Wilkins Co., Baltimore, Md., USA.
13. Bottger, 1990, *Clin. Chem.* 36: 1258-1259.
14. Corless et al., 2000, *J. Clin. Microbiol.* 38: 1747-1752.
15. Lyons et al., 2000, *J. Clin. Microbiol.* 38: 2362-2365.
16. Schmidt et al., 1991, *BioTech.* 11: 176-177.
17. Bennet, C. L. and Frommer, M., 1997, *Insect. Mol. Biol.* 6: 343-356.
18. Altschul et al., 1997, *Nucl. Acids Res.* 25:3389.
19. Ausubel et al., "Current Protocols in Molecular Biology" John Wiley & Sons Inc, 1994-1998, Chapter 15.
20. Bonner and Laskey, 1974, *Eur. J. Biochem.* 46: 83.
21. Marmur and Doty, 1962, *J. Mol. Biol.* 5: 109.
22. Devereux et al., 1984, *Nucleic Acids Res.* 12: 387-395.
23. Altschul et al., 1990, *J. Mol. Biol.* 215:403-410.
24. Syed and Loesche, 1972, *Appl. Microbiol.* 26: 459-465.

The invention claimed is:

1. A method for determining total microbial content in a sample, said method comprising amplifying a target sequence selected from 16S rDNA and 16S rRNA using as a forward primer, an oligonucleotide comprising the sequence set forth in SEQ ID NO: 1 and using as a reverse primer, an oligonucleotide comprising the sequence set forth in SEQ ID NO: 2, said amplification being for a time and under conditions sufficient to generate a level of an amplification product which is proportional to the level of microorganisms in said sample.

2. The method of claim 1 wherein the amplification product is detected by hybridizing a probe to a nucleotide sequence nested between said forward and reverse primers.

3. The method of claim 1 or 2 wherein the target sequence is 16S rDNA.

4. The method of claim 1 or 2 wherein the target sequence is 16S rRNA.

5. The method of claim 1 or 2 wherein the sample is a biological, medical, agricultural, industrial or environmental sample.

6. The method of claim 5 wherein the medical sample is a culture fluid, biopsy fluid or tissue, swab or sample from oral cavity or other sample.

7. The method of claim 5 wherein the biological sample is from an animal or insect or plant.

8. The method of claim 7 wherein the medical sample is from an oral cavity.

9. The method of claim 5 wherein the sample is an environmental sample.

10. The method of claim 9 wherein the environmental sample is from soil, river, hot mineral springs, plant, antarctic, air or extraterrestrial samples as well as samples from industrial sites such as waste sites and areas of oil spills or aromatic or complex molecule contamination and pesticide contamination.

11. The method of claim 5 wherein the sample comprises food, food components, food derivatives and/or food ingredients including food products formed in the dairy industry such as milk.

12. The method of claim 5 wherein the sample is liquid, solid, slurry, air, vapour, droplet, aerosol or a combination thereof.

13. A method according to claim 1 wherein the amplification is by polymerase chain reaction (PCR).

14. The method of claim 1 or 2 wherein the amplification is by Real-Time PCR.

15. A method for identifying a microorganism by its genus in a sample, said method comprising subjecting DNA in said sample to Real-Time PCR using a primers-probe set which comprises primers selected to amplify DNA comprising 16S rDNA and a probe which hybridizes to a nucleotide sequence nested between said primers wherein said probe is either specific for said microorganism to be identified or which is subsequently identified by a genus-specific probe wherein the primers comprise a forward primer comprising the sequence set forth in SEQ ID NO: 1 and a reverse primer comprising the sequence set forth by SEQ ID NO:2.

16. The method of claim 15 wherein the amplified DNA is 16S rDNA.

17. The method of claim 15 wherein the genus-specific probe is also a species-specific probe.

18. The method of claim 15 or 17 wherein the probe is a polynucleotide having the sequence set forth in SEQ ID NO: 3.

19. The method of claim 15 wherein the 16S rDNA is amplified.

20. The method of claim 15 wherein the sample is a biological, medical, agricultural, industrial or environmental sample.

21. The method of claim 20 wherein the medical sample is a culture fluid, biopsy fluid or tissue, swab or sample from oral cavity or other sample.

22. The method of claim 20 wherein the biological sample is from an animal or insect or plant.

23. The method of claim 20 wherein the medical sample is from an oral cavity.

24. The method of claim 20 wherein the sample is an environmental sample.

25. The method of claim 24 wherein the environmental sample is from soil, river, hot mineral springs, plant, antarctic, air or extraterrestrial samples as well as samples from industrial sites such as waste sites and areas of oil spills or aromatic or complex molecule contamination and pesticide contamination.

26. The method of claim 20 wherein the sample comprises food, food components, food derivatives and/or food ingredients including food products formed in the dairy industry such as milk.

27. The method of claim 20 wherein the sample is liquid, solid, slurry, air, vapour, droplet, aerosol or a combination thereof.

28. The method of claim 2 wherein the probe is a polynucleotide having the sequence set forth in SEQ ID NO: 3.

* * * * *